US011330977B2

(12) United States Patent
Jensen et al.

(10) Patent No.: US 11,330,977 B2
(45) Date of Patent: *May 17, 2022

(54) DIGITAL VISUAL ACUITY EYE EXAMINATION FOR REMOTE PHYSICIAN ASSESSMENT

(71) Applicant: 1-800 CONTACTS, INC., Draper, UT (US)

(72) Inventors: Brent Jensen, Bluffdale, UT (US); Tighe Racicot, Herriman, UT (US); Chad Allen, West Jordan, UT (US); Scott Stromberg, Sandy, UT (US); Dustin Hurst, Lehi, UT (US); Rico Lujan, Herriman, UT (US)

(73) Assignee: 1-800 Contacts, Inc., Draper, UT (US)

( * ) Notice: Subject to any disclaimer, the term of this patent is extended or adjusted under 35 U.S.C. 154(b) by 246 days.

This patent is subject to a terminal disclaimer.

(21) Appl. No.: 16/572,397

(22) Filed: Sep. 16, 2019

(65) Prior Publication Data

US 2020/0069173 A1 Mar. 5, 2020

Related U.S. Application Data

(63) Continuation of application No. 15/838,029, filed on Dec. 11, 2017, now Pat. No. 10,413,172.

(51) Int. Cl.
*A61B 3/028* (2006.01)
*A61B 3/00* (2006.01)
(Continued)

(52) U.S. Cl.
CPC .......... *A61B 3/028* (2013.01); *A61B 3/0025* (2013.01); *A61B 3/0033* (2013.01);
(Continued)

(58) Field of Classification Search
CPC ....... A61B 3/028; A61B 3/032; A61B 3/0083; A61B 3/0033; A61B 3/0025; A61B 3/024;
(Continued)

(56) References Cited

U.S. PATENT DOCUMENTS 7,784,948 B2 8/2010 Nozawa et al.

OTHER PUBLICATIONS

International Search Report and Written Opinion for International Application No. PCT/US2018/064442 dated Jan. 24, 2019.

*Primary Examiner* — Tuyen Tra
(74) *Attorney, Agent, or Firm* — Dorsey & Whitney LLP

(57) ABSTRACT

Systems and methods for assessing the visual acuity of person using a computerized consumer device are described. The approach involves determining a separation distance between a human user and the consumer device based on an image size of a physical feature of the user, instructing the user to adjust the separation between the user and the consumer device until a predetermined separation distance range is achieved, presenting a visual acuity test to the user including displaying predetermined optotypes for identification by the user, recording the user's spoken identifications of the predetermined optotypes and providing real-time feedback to the user of detection of the spoken indications by the consumer device, carrying out voice recognition on the spoken identifications to generate corresponding converted text, comparing recognized words of the converted text to permissible words corresponding to the predetermined optotypes, determining a score based on the comparison, and determining whether the person passed the visual acuity test.

27 Claims, 15 Drawing Sheets

(51) Int. Cl.
*G06T 7/70* (2017.01)
*G10L 15/22* (2006.01)
*H04R 1/02* (2006.01)
*A61B 3/032* (2006.01)
*G10L 25/60* (2013.01)
*G10L 15/26* (2006.01)

(52) U.S. Cl.
CPC ............ *A61B 3/0083* (2013.01); *A61B 3/032* (2013.01); *G06T 7/70* (2017.01); *G10L 15/22* (2013.01); *H04R 1/028* (2013.01); *G10L 15/26* (2013.01); *G10L 25/60* (2013.01); *H04R 2400/00* (2013.01); *H04R 2410/00* (2013.01); *H04R 2499/15* (2013.01)

(58) Field of Classification Search
CPC . G06T 7/70; G10L 15/22; G10L 15/26; G10L 25/60; H04R 1/028; H04R 2400/00; H04R 2410/00; H04R 2499/15
See application file for complete search history.

DIGITAL VISUAL ACUITY EYE EXAMINATION FOR REMOTE PHYSICIAN ASSESSMENT

CROSS REFERENCE TO RELATED APPLICATION

This application is related to United States Utility Patent application Ser. No. 15/838,029, filed 11 Dec. 2017, entitled "DIGITAL VISUAL ACUITY EYE EXAMINATION FOR REMOTE PHYSICIAN ASSESSMENT,", now issued as U.S. Pat. No. 10,413,172, the entire contents of which are incorporated herein by reference.

BACKGROUND

Field of the Disclosure

The present disclosure relates to eye examinations and, in particular, to computer-based visual acuity examinations carried out without the use of optical refractor lens assemblies.

Background Information

Myopia, hyperopia, and astigmatism are common refractive errors of the eye that afflict many people. Myopia, typically referred to as nearsightedness, is a refractive defect of the eye in which images are focused forward of the image surface of the retina. Hyperopia, typically referred to as farsightedness, is a refractive defect of the eye in which images are focused in behind the image surface of the retina. Astigmatism is a refractive defect of the eye stemming from an imperfection in spherical curvature of the optical system of the eye in which parallel rays of light are focused onto two different points rather than one common point at the image surface of the retina.

People traditionally have visited an eye doctor personally in the eye doctor's office in order to obtain diagnosis of such eye conditions as well as a prescription for purchasing corrective lenses such as contact lenses or spectacles. Such in-person visits to eye doctors may be costly and time consuming, for example, by requiring an individual to take time away from work or from other obligations and travel to the location of the eye doctor's office to receive an eye examination.

Computerized eye examinations that do not require an in-person visit with an eye doctor have arisen in part to address issues of the time-consuming nature and cost of traditional, in-person eye examinations with an eye doctor. However, the present inventors have observed that existing computerized eye examinations themselves may be overly complex and time consuming, and may provide less than optimal customer experience arising out of technical deficiencies in conventional computerized eye examinations. The present disclosure provides technological solutions to such technological problems in computerized eye examinations.

SUMMARY

The present inventors have observed that existing computerized eye examinations that may be taken with a personal computing device without in-person administration by an eye doctor may be overly complex and time consuming and may provide an unsatisfactory consumer experience should the computerized eye examination need to be retaken because of technical deficiencies such as insufficient examination results data, ambiguous examination results data, lack of verification of conditions suitable for unassisted computerized eye examination, and lack of technical feedback to the user during the computerized eye examination. These challenges arise in a technological context in computerized eye examinations and are not encountered with traditional in-person eye examination administered by an eye doctor using a traditional refractor lens assembly of the type commonly found in eye doctor offices.

The present disclosure may provide technical solutions to these technological problems by providing a computerized eye examination, e.g., a visual acuity examination taken with the user wearing corrective lenses of an existing prescription, and taken with a personal consumer computing device such as a laptop computer, tablet computer, smart phone, etc., without the need for administration of the exam by an in-person eye professional, wherein the computerized eye exam provides real-time user feedback during the eye examination to enhance the reliability of eye examination data obtained and by using sophisticated processing of eye examination data obtained by the personal computing device, either during the eye examination or promptly thereafter, to enhance the reliability of processed eye examination data. Exemplary approaches described herein may further provide screening of obtained eye examination data by a human technician at a remote computer system and further review of the (screened) eye-examination data by a physician, who may reissue the prescription to permit the user to complete an online purchase of corrective lenses such as contact lenses or spectacles, and who may also assess the eye-examination data for any concerns and potentially recommend an in-person eye examination with a physician for further assessment.

According to one exemplary aspect, a method for testing visual acuity of a user using a computerized consumer device is described. The computerized consumer device includes a display screen, a camera, a microphone, a speaker, a computer processor, and a memory, and may be, e.g., a tablet computer, a smart phone, a personal computer such as a desktop, laptop or notebook computer, or the like. The user is a human subject. The method includes: initiating a visual acuity test to assess the visual acuity of a user using a computerized consumer device, the computerized consumer device, the user being a human subject; determining, by the computerized device, a separation distance between a user and the computerized consumer device based on an image size of a physical feature of the person using imagery of the user taken by the camera of the computerized consumer device; instructing, by the computerized consumer device, the user to adjust the separation between the user and the computerized consumer device, and instruct the user that a predetermined separation distance range is achieved; presenting, by the computerized consumer device, a visual acuity test to the user without use of a refractor lens assembly, wherein presenting the visual acuity test comprises displaying predetermined optotypes at the display screen of the computerized consumer device for the user to perceive; recording, at the computerized consumer device, spoken identifications by the user of perceptions of the optotypes via the microphone of the computerized consumer device, and providing real-time feedback to the user of detection of the spoken indications by the computerized consumer device; carrying out voice recognition on the user's spoken identifications to generate converted text corresponding to the spoken identifications; comparing recognized words of the converted text to permissible words corresponding to the predetermined optotypes using a lookup table; determining a score for visual acuity test taken by the user based on said comparing; and determining whether the user passed the visual acuity test based on the score.

According to another exemplary aspect, a consumer-based system for carrying out a visual acuity test of a user is described. The system comprises a computerized consumer device that includes a display screen, a camera, a microphone, a speaker, a computer processor, and a memory, and may be, e.g., a tablet computer, a smart phone, a personal computer such as a desktop, laptop or notebook computer, or the like. The user is a human subject. The system may also include one or more servers computers that may access one or more databases to store and permit access to test results of vision tests taken by multiple users, as well as remote computer systems for use by medical professionals, e.g., screening technicians and physicians, for review and assessment of vision test data and results, e.g., for approval of vision test results in order to permit renewing the eye prescriptions of users so that users may proceed to make online purchases of corrective lenses such as contact lenses or spectacles. The computer processor is configured to cause the computerized consumer device to: initiate a visual acuity test to assess the visual acuity of a user using the computerized consumer device, the user being a human subject; determine a separation distance between a user and the computerized consumer device based on an image size of a physical feature of the person using imagery of the user taken by the camera of the computerized consumer device; instruct the user to adjust the separation between the user and the computerized consumer device, and instruct the user that a predetermined separation distance range is achieved; present a visual acuity test to the user without use of a refractor lens assembly, wherein presenting the visual acuity test comprises displaying predetermined optotypes at the display screen of the computerized consumer device for the user to perceive; record spoken identifications by the user of perceptions of the optotypes via the microphone of the computerized consumer device, and provide real-time feedback to the user of detection of the spoken indications by the computerized consumer device; carry out voice recognition on the user's spoken identifications to generate converted text corresponding to the spoken identifications; compare recognized words of the converted text to permissible words corresponding to the predetermined optotypes using a lookup table; determine a score for visual acuity test taken by the user based on said comparing; and determine whether the user passed the visual acuity test based on the score.

According to another exemplary aspect, a non-transitory computer readable medium comprising program instructions for permitting a computerized consumer device to carry out a visual acuity test of a user is described. The computerized consumer device includes a display screen, a camera, a microphone, a speaker, a computer processor, and a memory, and may be, e.g., a tablet computer, a smart phone, a personal computer such as a desktop, laptop or notebook computer, or the like. The user is a human subject. The program instructions are configured to, when executed, causing a computer processor of the computerized consumer device to: initiate a visual acuity test to assess the visual acuity of a user using the computerized consumer device, the computerized consumer device including a display screen, a camera, a microphone, a speaker, a computer processor, and a memory, the user being a human subject; determine a separation distance between a user and the computerized consumer device based on an image size of a physical feature of the person using imagery of the user taken by the camera of the computerized consumer device; instruct the user to adjust the separation between the user and the computerized consumer device, and instruct the user that a predetermined separation distance range is achieved; present a visual acuity test to the user without use of a refractor lens assembly, wherein presenting the visual acuity test comprises displaying predetermined optotypes at the display screen of the computerized consumer device for the user to perceive; record spoken identifications by the user of perceptions of the optotypes via the microphone of the computerized consumer device, and provide real-time feedback to the user of detection of the spoken indications by the computerized consumer device; carry out voice recognition on the user's spoken identifications to generate converted text corresponding to the spoken identifications; compare recognized words of the converted text to permissible words corresponding to the predetermined optotypes using a lookup table; determine a score for visual acuity test taken by the user based on said comparing; and determine whether the user passed the visual acuity test based on the score.

According to another exemplary aspect, a method for testing visual acuity of a user using a graphical interface and an audio interface at a computerized consumer device is described. The method comprises: initiating a visual acuity test to assess the visual acuity of a user using a computerized consumer device, the computerized consumer device comprising a display, a camera, an audio interface including a microphone and a speaker, a computer processor, and a memory, the user being a human subject, the visual acuity test comprising a graphical interface for displaying information to the user and for receiving input from the user via touch sensitive fields; displaying, via the graphical interface, distance information of a measured distance between the computerized consumer device and the user measured from imagery of the user captured by the camera of the computerized consumer device to thereby provide guidance to the user to move to a desired predetermined distance range, the graphical interface being configured to dynamically display the distance information in real time as the measured distance changes; displaying, via the graphical interface, the visual acuity test without use of a refractor lens assembly including displaying predetermined optotypes for the user to perceive, and presenting audio instructions for the visual acuity test via the speaker of the audio interface; recording, via the microphone of the audio interface, spoken identifications by the user of perceptions of the predetermined optotypes, and providing real-time visual feedback to the user via the graphical interface indicative of detection of the spoken indications by the computerized consumer device; carrying out speech recognition on the user's spoken identifications to generate converted text corresponding to the spoken identifications; comparing recognized words of the converted text to permissible words corresponding to the predetermined optotypes using a lookup table; determining a score for visual acuity test taken by the user based on said comparing; and determining whether the user passed the visual acuity test based on the score.

BRIEF DESCRIPTION OF THE FIGURES

These and other features, aspects, and advantages of the present disclosure will become better understood with regard to the following description, appended claims, and accompanying drawings.

FIGS. 4-6 illustrate exemplary introductory screens (which may also be referred to as pages) of a graphical interface (also referred to as a graphical user interface or GUI) for a vision test presented via an application (or app) at a display screen of a computerized consumer device 400, such as a tablet or a smart phone, according to an example.

FIGS. 7-10 illustrate exemplary GUI screens of the app for entering patient information, according to an example.

DETAILED DESCRIPTION OF EXEMPLARY EMBODIMENTS

The present inventors have developed approaches for conveniently and reliably conducting vision tests (or examinations) using a computerized consumer device (or consumer computing device) such as a tablet computer, smart phone, personal computer such as a laptop computer, desktop computer, notebook computer, and the like. Vision test results may be communicated to medical professionals, such as screening technicians and physicians at remote computer systems, for review and assessment, such as described via examples herein. Such vision tests, including visual acuity tests and eye surface imaging, can be carried out, for instance, in one's own home or other location without the need to travel to a doctor's office for an in-person eye examination with an eye doctor, and as described herein, may provide advantages over conventional computerized vision tests by providing real-time feedback to the users during the tests to enhance the user experience, reduce complexity, and promote the gathering of reliable test data. Such tests can provide convenience and lower cost and can be particularly desirable for confirming the accuracy of existing (though perhaps expired) lens prescriptions to facilitate the online purchase of corrective lenses using the most recent lens prescription.

Figure 1:
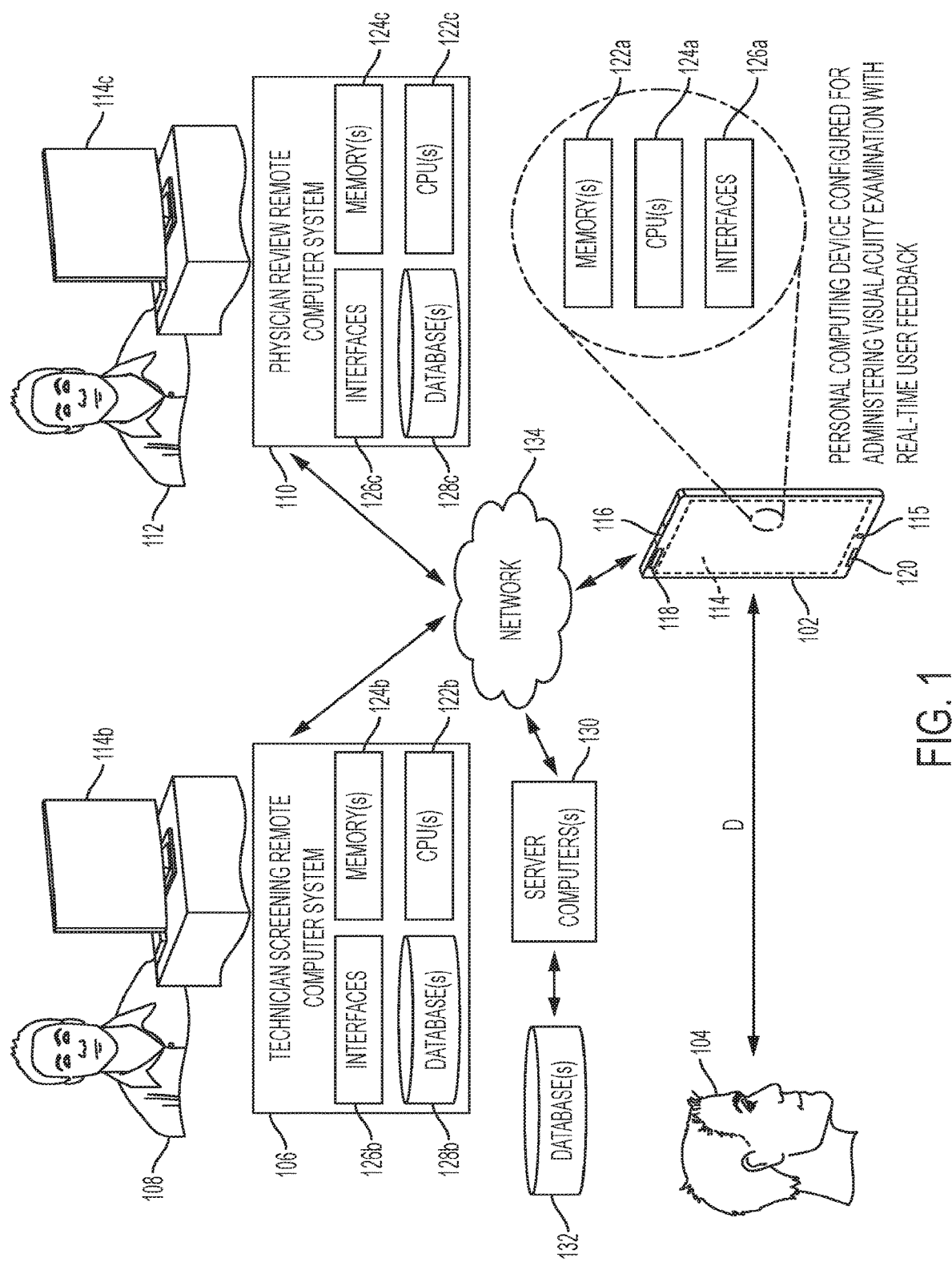
FIG. 1 illustrates an exemplary framework for conducting a computerized eye examination with a computerized consumer device according to an exemplary aspect.

FIG. 1 illustrates an exemplary framework for conducting a computerized eye examination with a computerized consumer device according to an exemplary aspect. As shown in FIG. 1, a computerized consumer device 102, such as a tablet computer, a smart phone, or a personal computer such as a laptop computer, desktop computer, or notebook computer may present one or more vision exams to a user 104, who is a human subject. Computerized consumer device 102 may also be, for example a gaming device or other multimedia device. Computerized consumer device 102 may include a touch sensitive display screen (which may also be referred to as a touchscreen display) 114, a speaker 116 that projects audio, a camera 118 (including a lens, lens cover, image sensor, and camera circuitry), and a microphone 120 that permits collection of speech generated by the user. Vision tests may be presented to the user 104 via the display screen 114 in the form of a series of screens (or pages) of a graphical interface (also referred to as a graphical user interface or GUI) that present various test elements and instructions to the user, and that prompt the user for responses or instruct the user to take certain actions. While one camera 118 is shown in FIG. 1, two or more forward-facing cameras, i.e., cameras positioned at a same side of the display screen 114 may be provided at the consumer device 102, e.g., spaced apart from one another, e.g., at opposing edges of the consumer device 102, as to be able to obtain imagery of the user simultaneously from two or more different angles or orientations relative to the user. Also, one more additional rear-facing cameras may be provided at a side of the consumer device 102 opposite the display screen 114. For example, speaker 116 and display screen (or touchscreen display) 114 may both present instructions to the user 104, and touchscreen display 114 and microphone 120 may be used to record user responses or input to various vision test elements or instructions.

Data gathered during the vision testing by computerized consumer device 102 may be processed by device 102 and further communicated to remote computer systems 106 and 110 via a network 134 such as the Internet. In this regard, any suitable combination of wireless and wired communication may be used, e.g., Wi-Fi, Bluetooth, etc. Remote computer system 106 may serve as a technician screening system operated by a technician 108, who may screen vision test data acquired by the computerized consumer device 102 via a display 114b. Computerized consumer device 102 and remote computer systems 106 and 110 may access data from and communicate data to one or more server computers 130 which may access one or more databases 132 for storing data in any desired format. Remote computer system 110 may serve as a physician review computer's system operated by a physician 112, who may review via a display 114c the vision test data, including imagery of the user's eyes, acquired by computerized consumer device 102 as well as screening results generated by the technician 108 that have been stored and are accessible by the physician remote computer system 110 via the network 134. In examples, in addition to, or instead of, display screens 114b and 114c (each of which may comprise multiple display screens), the physician 112 and technician 108 may view imagery of the user's eyes using display devices such as virtual reality (VR) goggles, imagery-display headsets, and three-dimensional (3D) vision enhancement devices configured to operate in conjunction with displays 114b, 114c or other displays, e.g., to permit stereoscopic or multiscopic viewing of eye surface imagery with three-dimensional (3D) depth perception of such imagery (where eye surface imagery is obtained simultaneously from two or more different directions with multiple forward facing cameras 118 of the consumer device 102).

The computerized consumer device 102 includes a computer processor 122a, which may include one or more computer processing units (CPUs), and which can be any suitable combination of general purpose and special purpose processors. The consumer device 102 also includes one or more memories 124a, which may include RAM, ROM, and any suitable nonvolatile memory. Memory 124a may be used to store the instructions that execute the vision test app, data entered by the user, vision test results generated by the vision test app, as well as any associated metadata. The computerized consumer device 102 may also include one or more interfaces 114a to facilitate communication via networks including the Internet and for facilitating input/output of data, e.g., cellular communication transceiver, Wi-Fi transceiver, Bluetooth transceiver, as well as wired interfaces for communication and peripheral connection. It will be appreciated that the combination of speaker 116 and microphone 120 along with associated circuitry may comprise an audio user interface that permits the user 104 to both perceive audio data from the computerized consumer device 102 and provide audio data to the computerized consumer device. Computerized consumer device 102 also includes a GPS (mobile positioning system) receiver for detecting a location of the consumer device 102.

Likewise, remote computer system 106 (e.g., technician screening computer) includes a computer processor 122b, which may include one or more CPUs, one or more memories 124a, which may include RAM, ROM, and any suitable nonvolatile memory, and one or more interfaces 114a to facilitate communication via networks including the Internet and for facilitating input/output of data. Remote computer system 106 may also include one or more database(s) 128b to facilitate the storing of data in desired formats. Similarly, remote computer system 110 (e.g., physician review computer) includes a computer processor 122c, which may include one or more CPUs, and one or more memories 124c, which may include RAM, ROM, and any suitable nonvolatile memory, one or more interfaces 114c to facilitate communication via networks including the Internet and for facilitating input/output of data, and one or more database(s) 128c to facilitate the storing of data in desired formats.

Remote computer systems 106 and 110 may store a variety of data in memories 124b, 124c and databases, 128b, 128c and 132 to support the administration, execution, processing, and review of vision tests as described herein. Such data may include, for example, medical history information of users 104, vision test results users 104, processed data generated by remote analysis and processing of vision test results of users 104, imagery acquired from vision tests for users 104 including video imagery and still imagery, GPS location data associated with users 104, screening comments and determinations made by screening technician 108, physician review comments and determinations made by physician 112, and the like.

Exemplary approaches for exemplary vision testing using a computerized consumer device will now be described with reference to FIGS. 2 and 3 and with further reference to FIGS. 4-27. In this example, GUI screens and audio instructions of a vision test app are presented via a display screen 114 and speaker 116 of a computerized consumer device 102, such as a tablet or a smart phone as previously mentioned, and user 104 input is recorded via the touchscreen display 114 and via the microphone 120, which receives the user's spoken responses. While this example describes conducting an eye-surface imaging test as well as a visual acuity test using displayed optotypes (optical characters or symbols used in vision testing), additional tests could also be carried out, such as, for example, a color blindness test such as an Ishihara color blindness test known in the art.

In addition to the steps described below, it may be desirable to take preliminary steps to enhance the experience of the user. For example, according to some aspects, it may be advantageous to temporarily defeat or suspend certain functionality at the consumer device 102 including the following so that such functionality is not executed during testing: automatic brightness control of the display screen 114 that might otherwise result in unwanted screen dimming; automatic screen saver functionality that might otherwise change the screen; automatic popup messaging that might obscure GUI screens of the test; and the like. It will be appreciated that GUI screens may be presented to the user 104 at the consumer device 102 so that the user can grant permission for the vision test app to execute these temporary changes.

Figure 2:
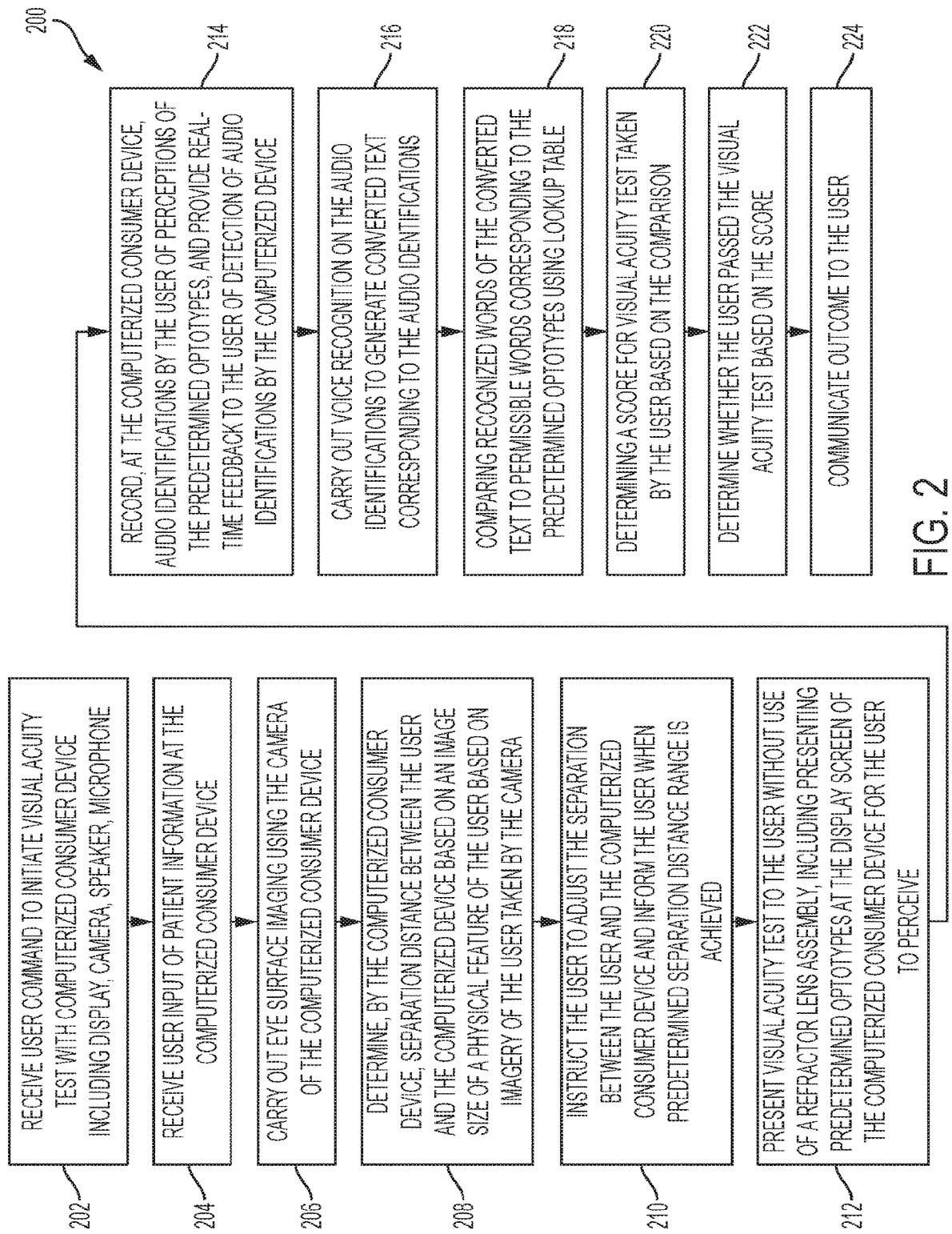
FIG. 2 illustrates a flow diagram for an exemplary approach for carrying out a computerized eye examination including a visual examination with a computerized consumer device according to an exemplary aspect.
Figure 5:
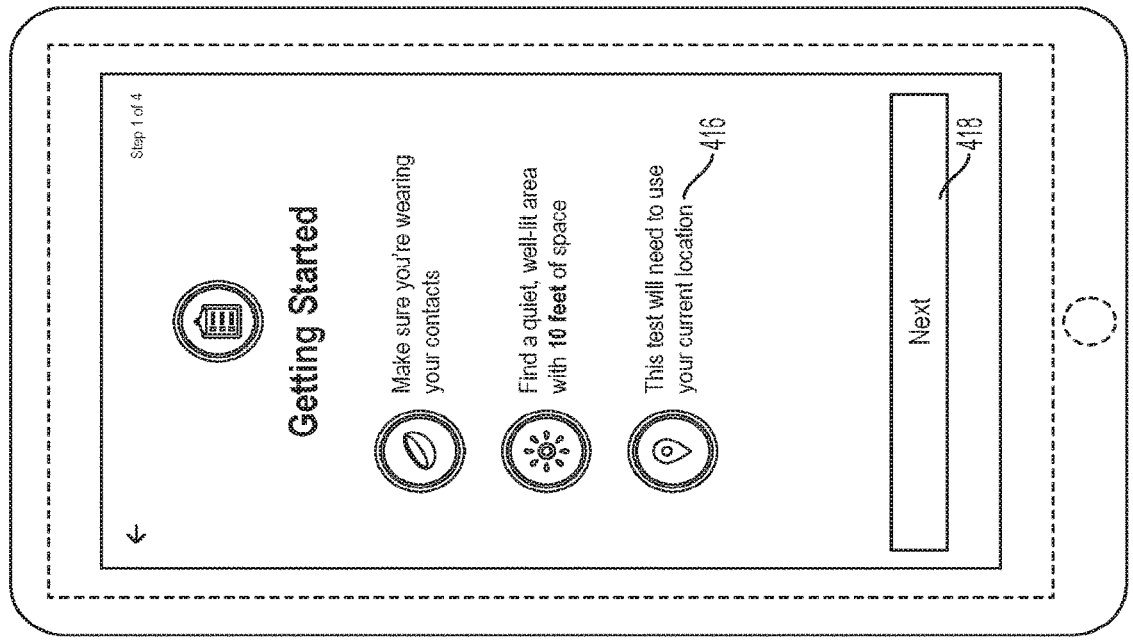
Figure 4:
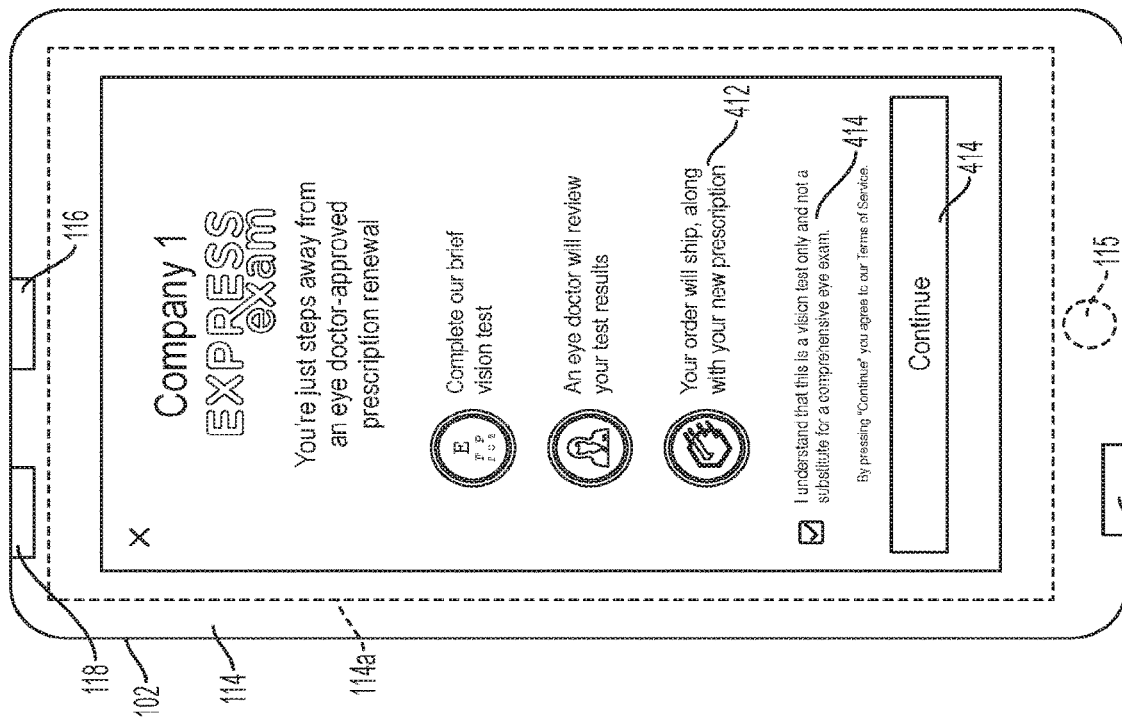

FIG. 2 illustrates a flow diagram for an exemplary approach for carrying out a computerized eye examination including a visual acuity examination with a computerized consumer device executing a vision testing application (app) according to an example. As shown at step 202, the computerized consumer device 102 receives a command to initiate a vision test including a visual acuity test. Exemplary GUI screens for initiating such vision testing using a vision test app according to this example are shown in FIGS. 4-5 (and FIG. 17). FIG. 4 illustrates an exemplary computerized consumer device 102 including touch screen display 114, speaker 116, camera 118, microphone 120, and control button 115, such as previously described. In addition, a display area of touchscreen display 114 is shown by a dotted line at 114a. FIG. 4 illustrates an exemplary first GUI screen of the app presented at display screen 114. As shown in FIG. 4, in this example, the screen is presented with a company name at the top, a name of the application (e.g., EXPRESS EXAM), and various introductory information identified by reference numeral 412. The GUI screen in FIG. 4 also includes an acknowledgment portion 414 with a check box to be checked by the user 104 to acknowledge the user 104 understands that the vision test being provided is not a substitute for a comprehensive eye exam. The initial GUI screen in FIG. 4 also includes a field 414 for the user to touch to continue the exam.

Figures 6, 7:
Figure 11:
FIGS. 11-16 illustrate exemplary GUI screens of the app for conducting eye surface imaging according to an example.
Figure 10:
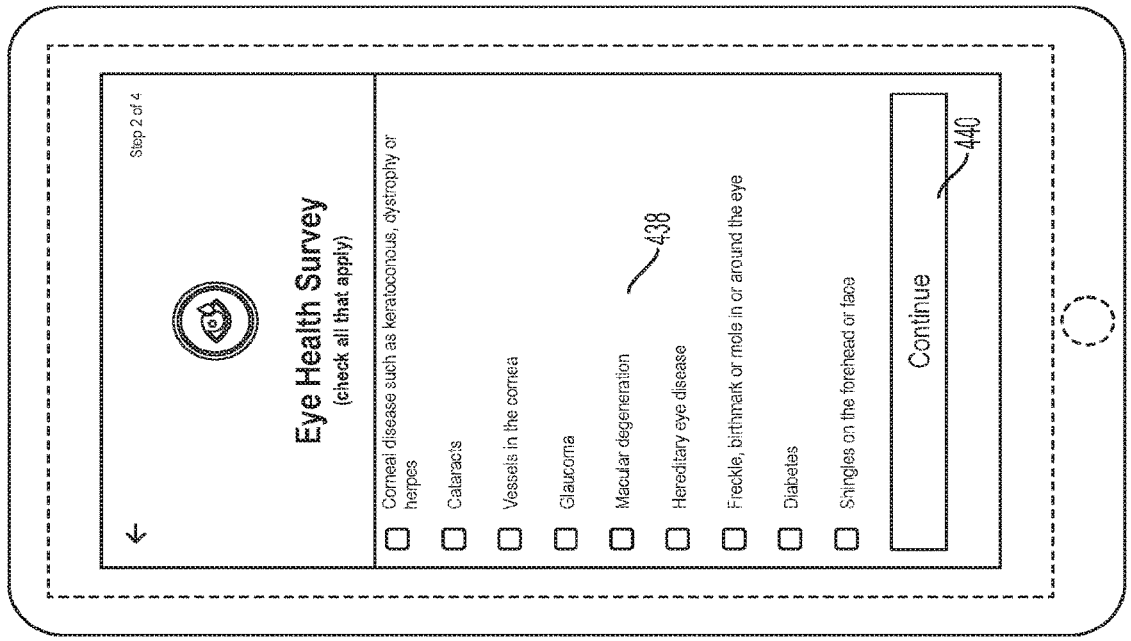
Figure 13:
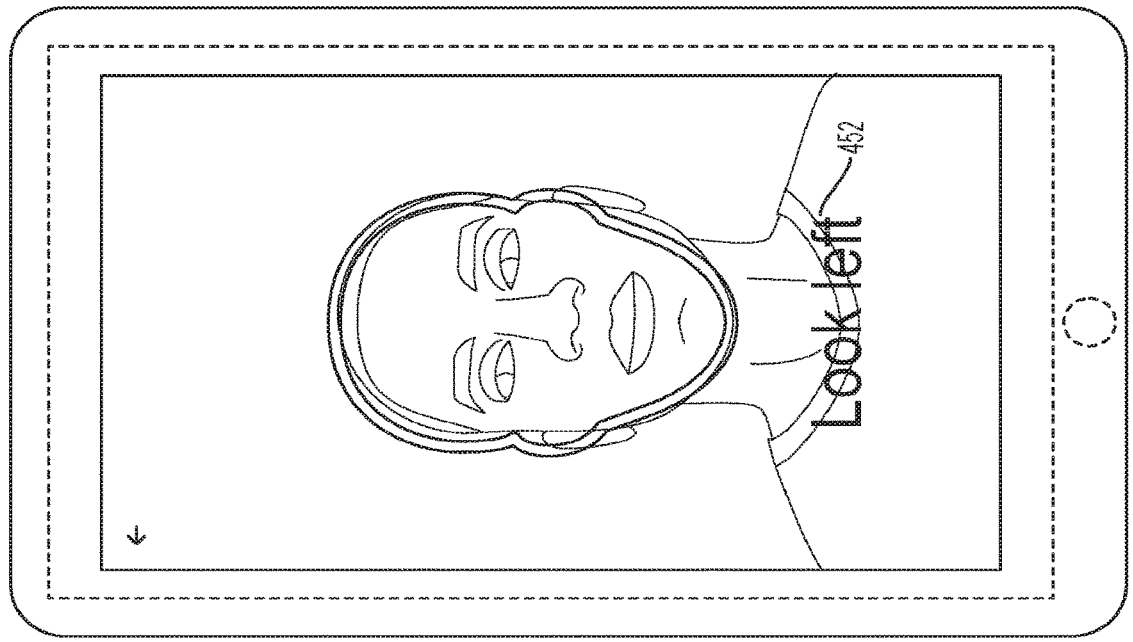

After touching the "continue" field 414, a GUI screen shown in FIG. 5 is displayed. This GUI screen includes an instruction portion 416 directing the user to make sure that the corrective lenses are presently being worn, to find a quiet, well-lit area with, e.g., 10 feet of available space, and to inform the user that the test will need to access the user's current location via GPS functionality. After pressing the "next" field 418 of the GUI, the app proceeds to display the GUI screen shown in FIG. 6. FIG. 6 shows an exemplary GUI screen that displays a map location 420 and that asks the user to confirm that the location is correct by pressing a "confirm location" field 422.

Returning to FIG. 2, at step 204, the computerized consumer device 102 may receive user input of the user's patient information. Exemplary GUI screens for this step of the vision test app are shown in FIGS. 7-10. The GUI screen shown in FIG. 7 includes an instruction portion 424 asking for the user's age, the approximate date of the last comprehensive eye exam, and gender (optional). This screen also includes data entry fields 426 that are responsive to user touch and permit the user to enter the data via a pop-up keypad or via drop-down menus, e.g., to select date information and gender, as may be appropriate, an exemplary result of which is shown in FIG. 8. Upon pressing the quote next unquote field 432, the app proceeds to display the GUI screen shown in FIG. 9. The exemplary GUI screen shown in FIG. 9 permits the user 104 to continue to enter patient information by indicating at checkbox field 434 whether the user has had an eye infection, had eye surgery, or used prescription eye drops since the last in person eye examination. The user 104 is also prompted to enter via checkbox field 436 (of FIG. 9) and checkbox field 438 (of FIG. 10) any listed conditions that the user 104 has experienced. In this regard field 438 represents a continuation of field 436 that the user may access by scrolling down word using a finger stroke against the touchscreen 114. After completion of the eye health survey illustrated in FIGS. 9-10, the user may advance to the next portion of the app by pressing the "continue" field 440.

Returning to FIG. 2, the method 200 includes at step 206 carrying out eye surface imaging using the camera 118 of the computerized consumer device 102. This eye surface imaging test (which may also be referred to, e.g., as an eye surface test or eye irritation test) may be carried out either before or after a visual acuity test and captures imagery of the user's eye surfaces using video imaging and/or still imaging to permit the physician 112 to evaluate any readily apparent conditions of concern, for example, excessive redness in the user's eyes. Exemplary GUI screens of the vision test app for carrying out this step are shown in FIGS. 11-16, and an exemplary flow diagram illustrating exemplary steps for the eye surface test is illustrated in FIG. 3. Details of the eye surface test associated with step 206 will be described later herein with reference to FIGS. 3 and 11-16.

Figure 17:
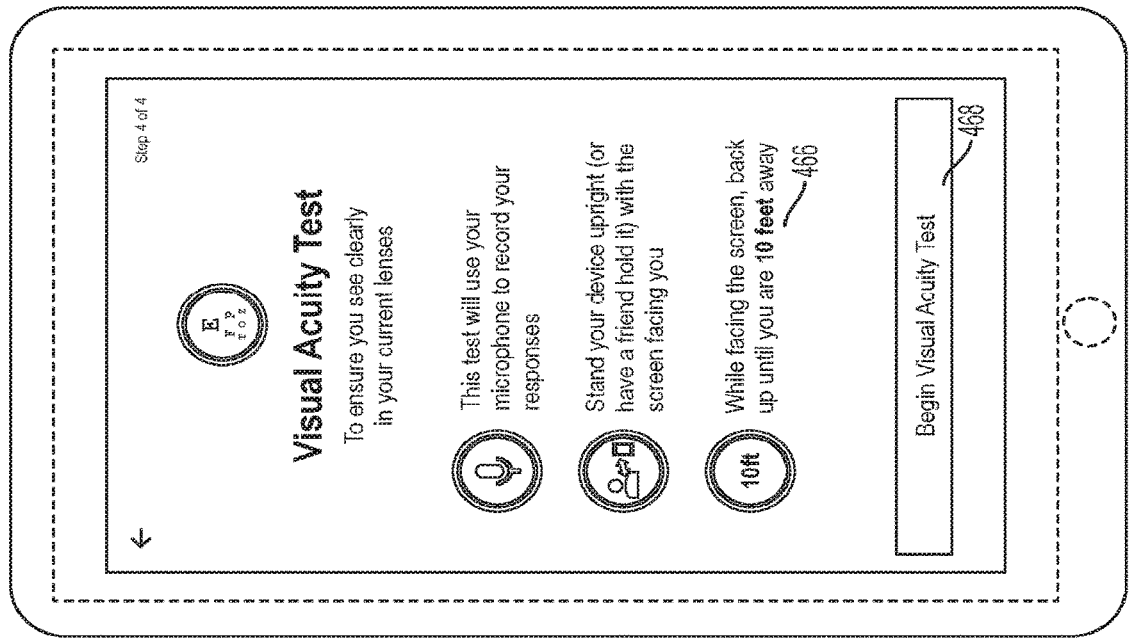
FIGS. 17-26 illustrate exemplary GUI screens of the app for conducting a visual acuity test, according to an example.

In the instant example, the visual acuity test can be conducted either before or after the eye surface test, and the visual acuity test can be initiated for example with the GUI screen shown in FIG. 17. As shown in FIG. 17, this GUI screen includes a message indicating to the user that the visual acuity test will now be carried out. This exemplary GUI screen also includes an information/instruction portion 466 informing the user that the test will use the microphone 120 to record the user 104 responses, and instructs the user visually via the display screen 114 to stand the consumer device 102 upright or have a friend hold it with the screen 114 facing the user 104. This exemplary GUI screen also instructs the user, while facing the screen 114, to back up until the user 104 is a predetermined distance, e.g., 10 feet, away from the consumer device 102. All these instructions can also be provided audibly via the speaker 116.

The user 104 may advance the vision test app to the actual vision test by touching the "begin visual acuity test field 468." Because the user 104 may have limited ability to accurately determine whether or not the user 104 is at the proper predetermined distance, the method 200 illustrated in FIG. 2 includes a step 208 of automatically determining by the computerized consumer device 102 in real-time the separation distance between the user and the computerized consumer device 102 based on an image size of the physical feature of the user based on imagery of the user taken by the camera 118.

More particularly, for example, the camera 118 may capture real-time imagery of the user, and the computer processor 122a of the computerized consumer device 102 may process that imagery in real-time to calculate a distance from the consumer device 102 to the user based on an image size of a physical feature whose actual physical size is either known or assumed known, e.g., in an average or median sense. An example is illustrated in the GUI screenshots shown in FIGS. 18-19, which illustrate the consumer device 102 determining the distance to the user 104 by carrying out facial detection processing and image analysis of the imagery to determine the apparent image size in pixels of the image sensor of the user's head (e.g., height, width, and/or area) or the pixel distance on the image sensor between the user's eye pupils. Thus, the distance determination may be based on imaging anatomical features of the user 104. Because the pupillary distance and head size have known average or median values, a calibration can be stored in the memory 124a of the consumer device 102 of the proper expected pixel distance between imaged pupils of the user's eyes or the proper expected image size in pixels of the user's head (e.g., width, height, and/or area). Referring to step 210, the consumer device 102 can instruct the user to adjust the separation between the user and the computerized consumer device 102 and inform the user that a predetermined separation distance range is achieved. In this regard, the separation distance between the user 104 in the consumer device 102 need not be precisely a desired predetermined value but may be within a range of accepted values such as within 10% of the a particular predetermined distance value, within 5% of the particular predetermined distance value, other percentage, or other threshold deviation from the particular predetermined distance value. When the real-time imaging and analysis of the measured size in pixels of a suitable physical feature (e.g., pupillary distance measured in pixels, or head size measured in pixels) matches the proper expected pixel values, the computer processor 122a of the consumer device 102 can cause the consumer device 102 to audibly inform the user 104 via the speaker 120 and/or visually inform the user via the display screen 114 that the user has reached the proper predetermined distance. Thus, for example, the separation distance can be determined simply with the computerized consumer device and without the use of an additional distance detection sensor or mechanism other than that provided by the camera and processing of imagery acquired by the camera as explained above.

Figure 12:
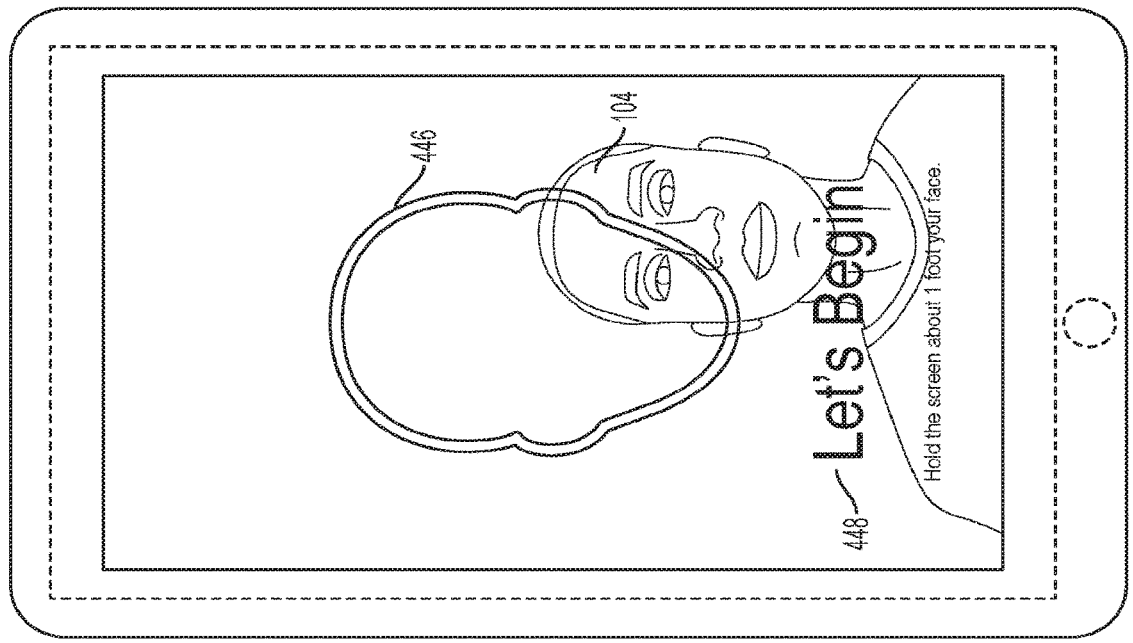
Figure 19:
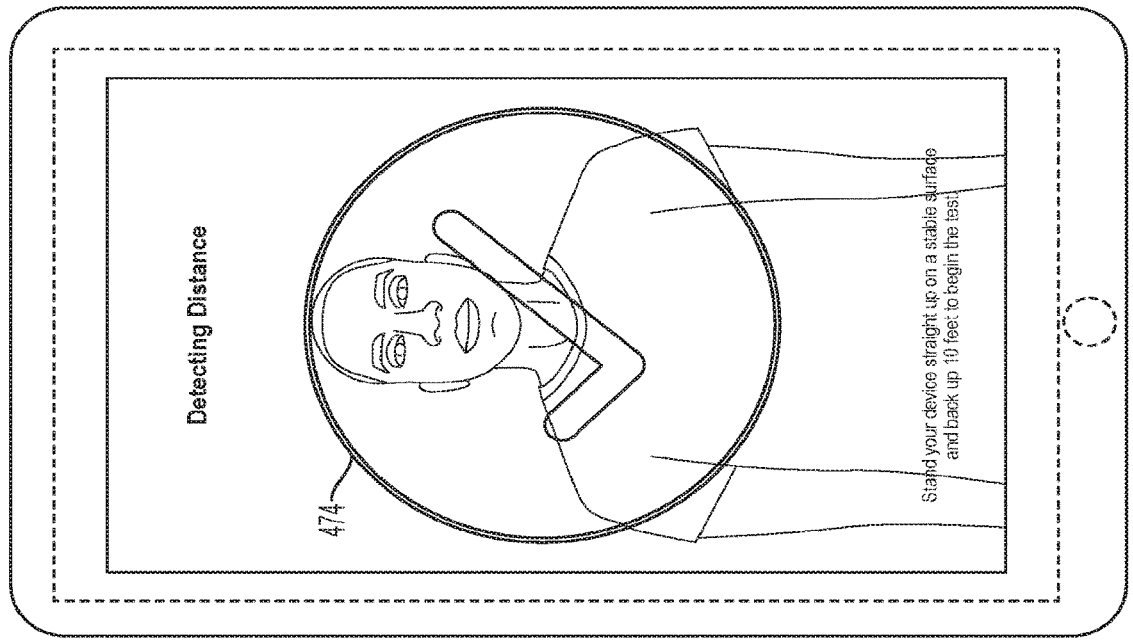
Figure 18:
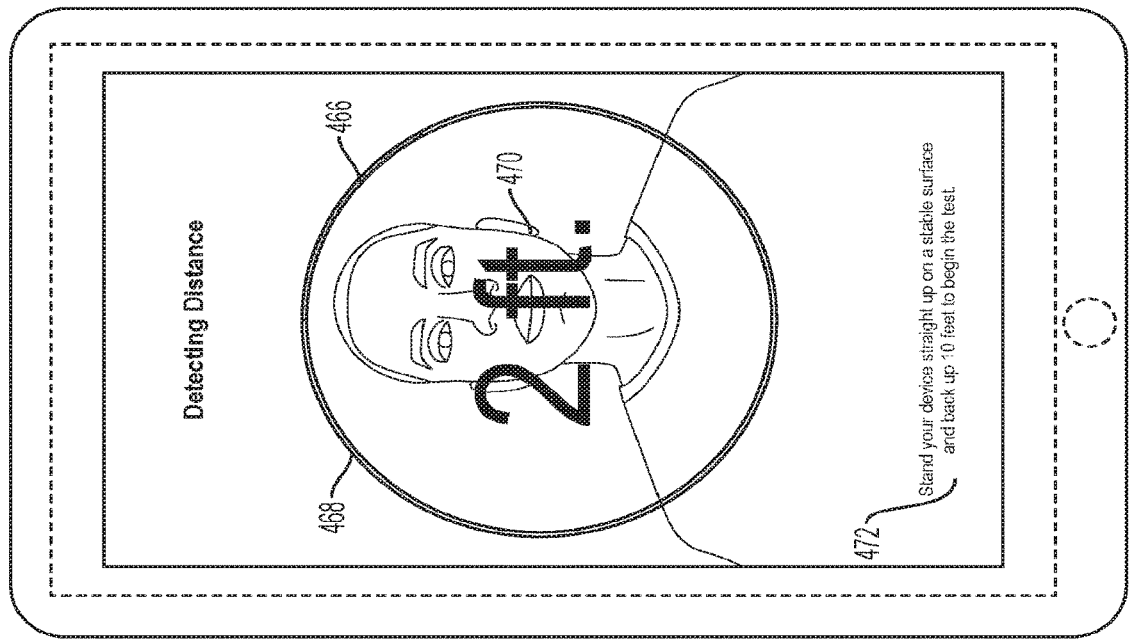
Figure 21:
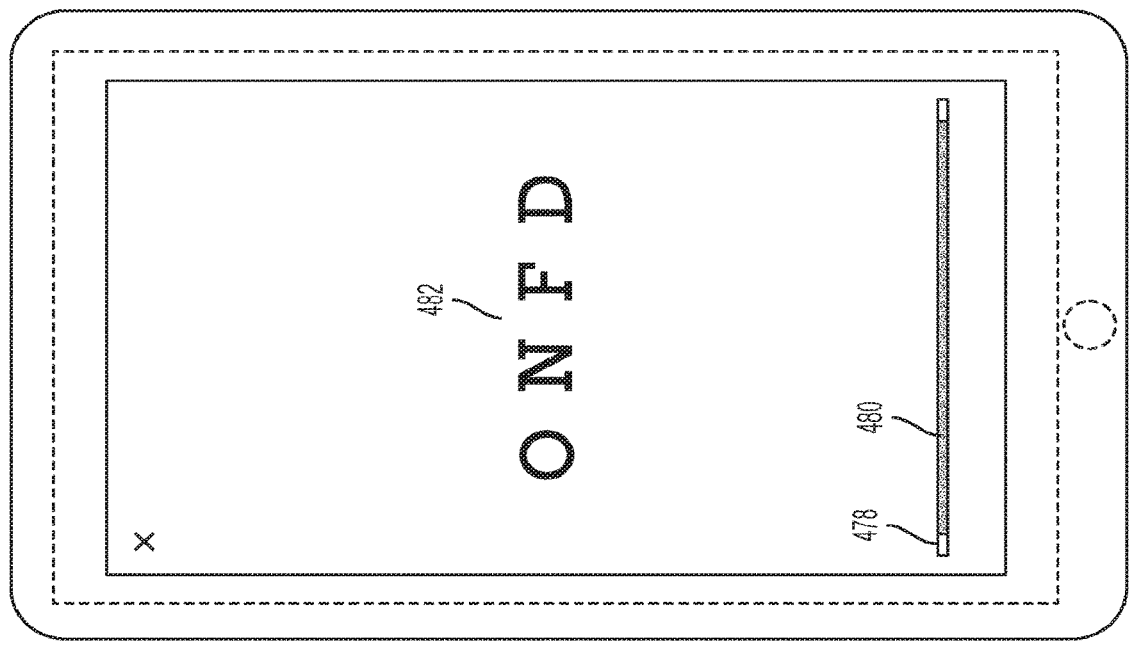

For example, as illustrated in FIG. 12, an instruction 472 to adjust position may be presented to the user 104 both visually on the display screen 114 as well as audibly via the speaker 116. In addition, for example, the detected image of the user may be displayed on the display screen 114 in real-time, and an indicator 468 such as a circle with a graphical meter portion 466 as well as a textual numerical distance indicator 470 may be displayed on the display screen 114 real-time as well to guide the user with real-time time feedback to the proper distance and proper orientation relative to the consumer device 102, e.g., so that the user's face is approximately centered on the display screen 114. Audio instructions may also be provided, e.g., such as "back up" or "too far." As shown in FIG. 19, when the proper distance has been obtained, and indicator 474 may be presented on the display screen 114 e.g., a checkmark in a circle, to indicate that the user has reached the proper distance, and/or an audible confirmation may be presented to the user via the speaker 116. Of course, the physical feature is not limited to anatomical features such pupillary distance between the user's eyes or the size of the user's head, and other physical features of known dimensions may also be used for this analysis, such as, a credit card or other object of known size held near the user's face or chest. In the latter case, suitable instructions may be provided to the user 104 to hold up a predetermined common object of known size.

Figure 20:
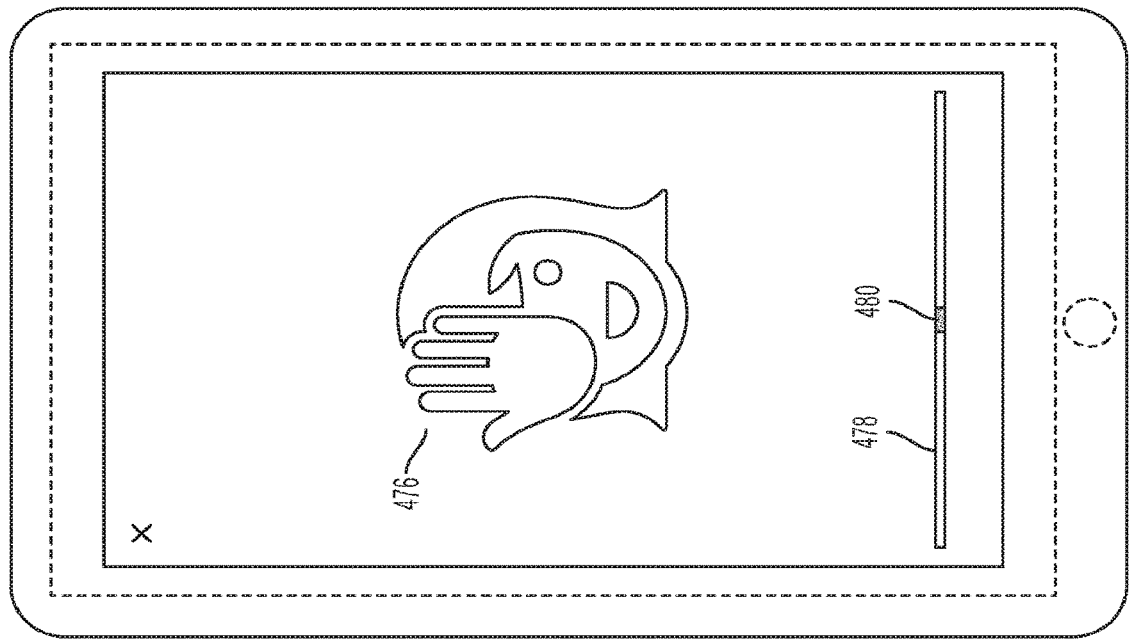
Figure 23:
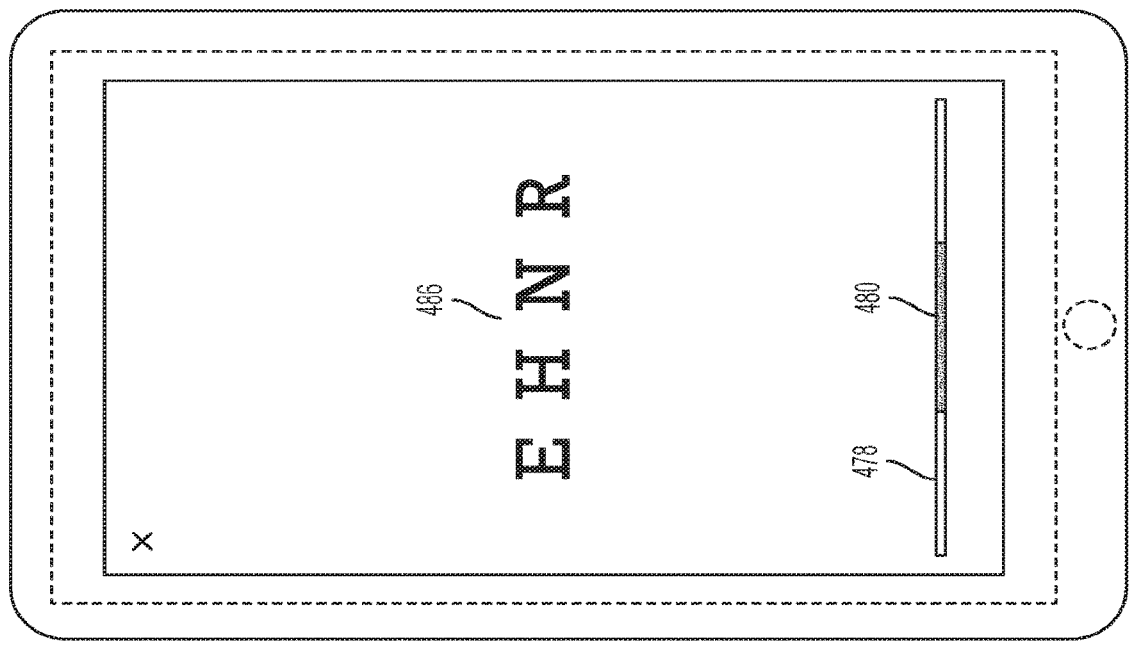

When the predetermined distance range has been achieved such as illustrated in FIG. 19, the consumer device 102 can automatically proceed to display optotypes on the display screen 114 to carry out the next portion of the visual acuity test. In this regard, as noted at step 212, the consumer device 102 presents the visual acuity test to the user including presenting predetermined optotypes at the display screen 114 of the computerized consumer device 102 for the user 104 to perceive. The optotypes are presented for the user's perception without use of a refractor lens assembly of the type commonly seen in eye-doctor offices. Examples of GUI screens of the optotype portion of the visual acuity test are shown in FIGS. 20-25. As shown in FIG. 20, a GUI screen can be displayed on the display screen 114 presenting an instruction graphic 476 for the user to cover her right eye, and an audio instruction instructing the user to cover her right eye may also be presented at the same time via the speaker 116. The GUI screen at FIG. 20 also illustrates an audio indicator 478 graphically displayed on the display screen 114 with a portion 480 that indicates the ambient sound level detected via the microphone 120. The vision test app automatically proceeds to display the GUI screen shown in FIG. 21 which comprises an optotype portion 482 including one or more optotypes to be perceived by the user 104. The vision test app then audibly instructs the user 104 to read or identify the characters (or other optotypes as the case may be) displayed on the screen 114. Thus, for example, the presentation of the predetermined optotypes may be done solely with the display screen of the computerized consumer device and without the use of an additional separate and distinct screen or other object located elsewhere in proximity to the user for presenting the predetermined optotypes.

When the user 104 audibly reads her perceptions of the characters (or other optotypes) displayed, as noted at step 214 of FIG. 2, the consumer device 102 records the audio identifications by the user 104 of her perceptions of the predetermined optotypes. In addition, the consumer device 102 provides real-time feedback to the user indicating that the user's audio identifications were detected by the consumer device 102. This feedback can be provided, for example, by graphically displaying on the screen 114 the audio indicator 478 and the portion 480 that is proportional to the detected sound level of user's spoken audio identifications. In this way, the consumer device 102 provides real-time feedback to the user that the test is proceeding normally so as to avoid user confusion about whether or not the device 102 properly captured the user's spoken responses to the displayed optotypes.

Figure 22:
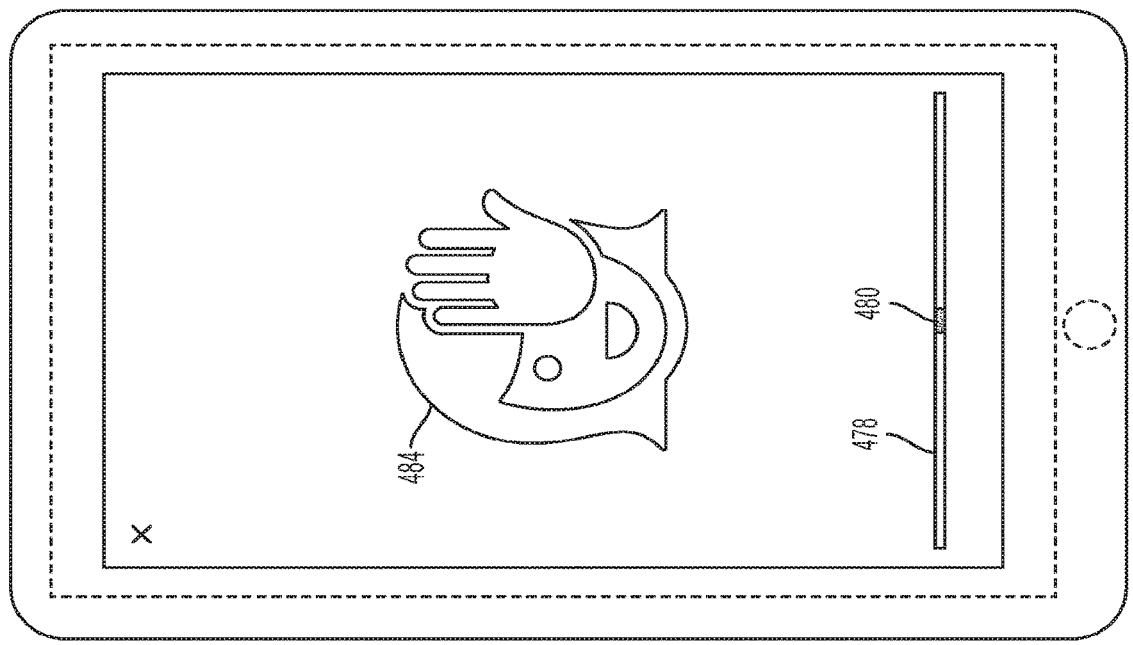
Figure 25:
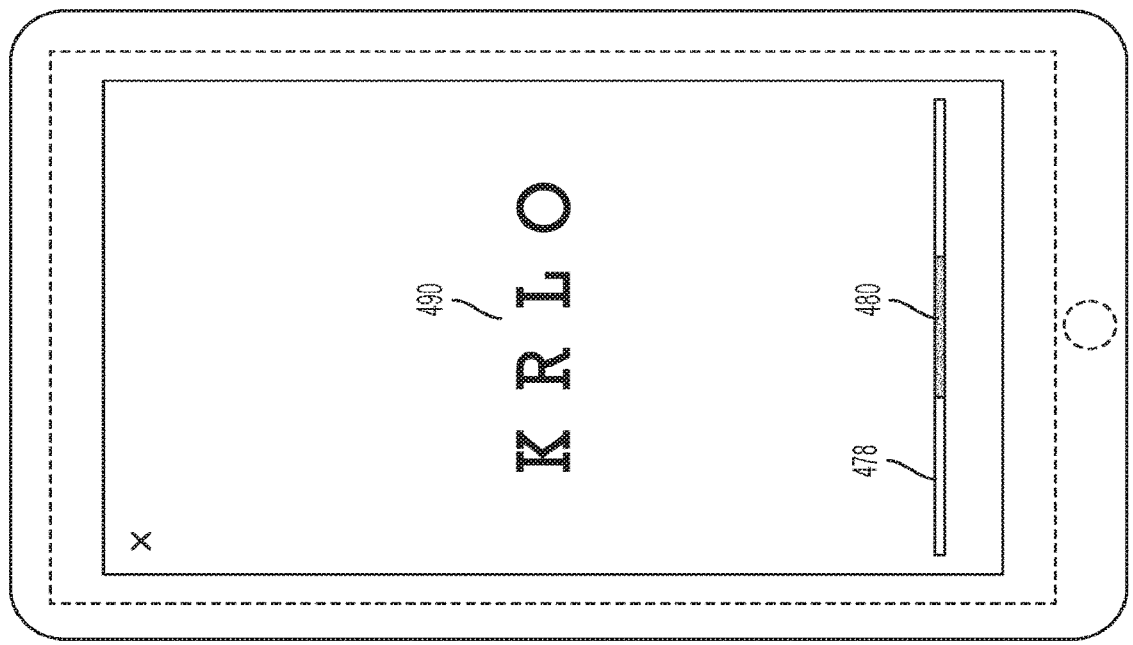
Figure 24:
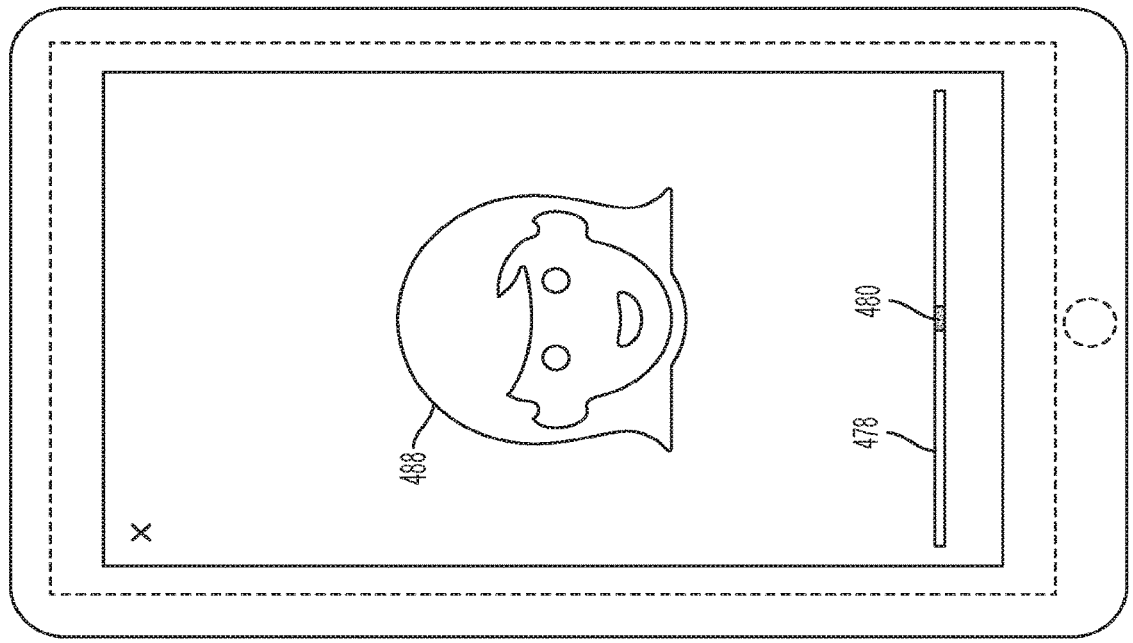
Figure 27:
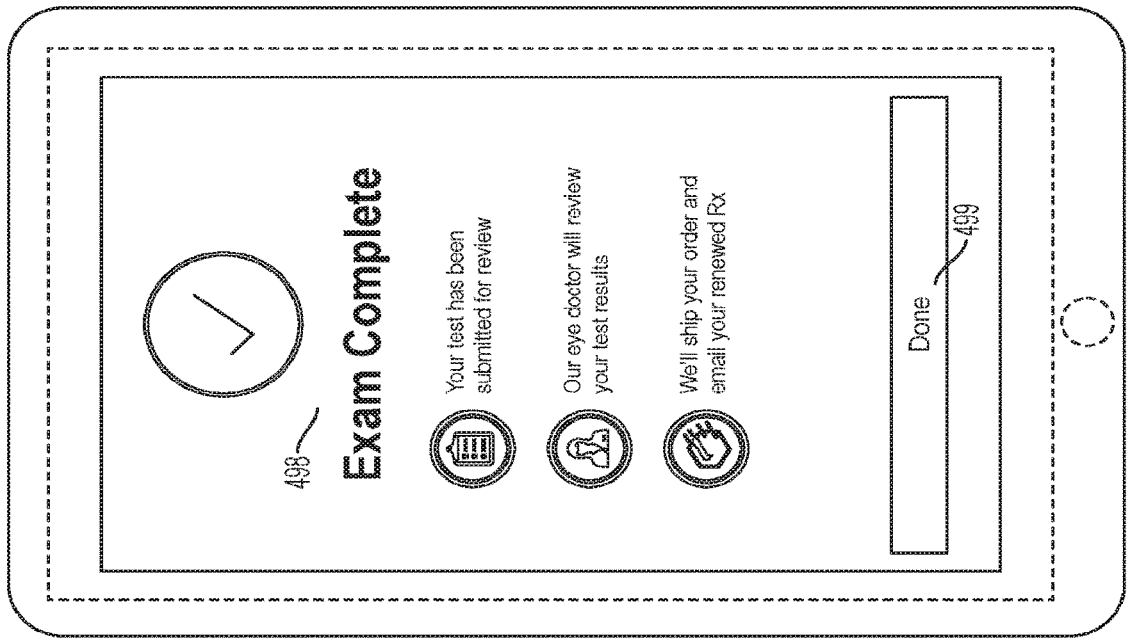
FIG. 27 illustrates an exemplary completion GUI screen of the app displayed at completion of the visual acuity test according to an example.

Thereafter, the vision test app automatically proceeds to display the exemplary GUI screen shown in FIG. 22, in which a new graphic 484 is displayed on the display screen 114 instructing the user 104 to cover the left eye. An audio instruction is also conveyed through the speaker 116 for the user 104 to cover the left eye, and an audio instruction is provided to the user 104 to read the optotypes shown at portion 486 of the display screen 114 in FIG. 23. The consumer device 102 likewise records the user 104 responses (step 214), and provides real-time sound level feedback to the user 104 via indicators 478 and 480, such as mentioned above. Thereafter, the vision test app automatically proceeds to display the exemplary GUI screen shown in FIG. 24, in which a new graphic 488 is displayed on the display screen 114 instructing the user to leave both eyes uncovered. An audio instruction is conveyed through the speaker 116 for the user 104 to leave both eyes uncovered, and an audio instruction is provided to the user 104 to read the optotypes shown at portion 490 of the display screen 114 in FIG. 25. The consumer device 102 likewise records the user 104 responses (step 214), and provides real-time sound level feedback to the user 104 via indicators 478 and 480, such as mentioned above.

The predetermined optotypes may be displayed at the display screen 114 of the computerized consumer device 102 in all instances is without changing a size of the predetermined optotypes displayed on the display screen 102 from a first size to a second size based on the separation distance between the user 104 and the computerized consumer device 102 as determined by the computerized consumer device 102. This is because the separation distance has already been achieved to which a predetermined distance range as explained previously. The sizes of the optotypes are configured to be consistent with proper visual acuity testing for the particular distance for which the visual acuity test is configured, but there is no need for dynamic changes to the sizes of the optotypes based on measured distance between the user 104 and consumer device 102.

As will be appreciated, various optotypes may be used for the visual acuity testing, including, but not limited, Snellen optotypes such as those described above. Any suitable optotypes may be used, for example, Landolt C optotypes, which comprise a sequence of broken rings with gaps presented in different directions (e.g., up, down, left, right) can also be used, "tumbling E" optotypes, which comprise "E" shaped symbols with the "fingers" thereof pointing, for a given orientation, in an associated direction, e.g., left, right, up, or down, geometric symbols (e.g., circle, square, triangle, star, diamond, etc.), mathematical symbols (e.g., divided by, plus, times, minus), common objects (ball, scissors, pencil, etc.), fruits (e.g., apple, banana, pear, strawberry, etc.), animal shapes, or any other suitable shapes that may service as distinctive symbols for use as optotypes. or other optotypes presently known in the art or later developed. Suitable lookup tables may be created for suitable optotypes such as taught by examples discussed below.

Figure 26:
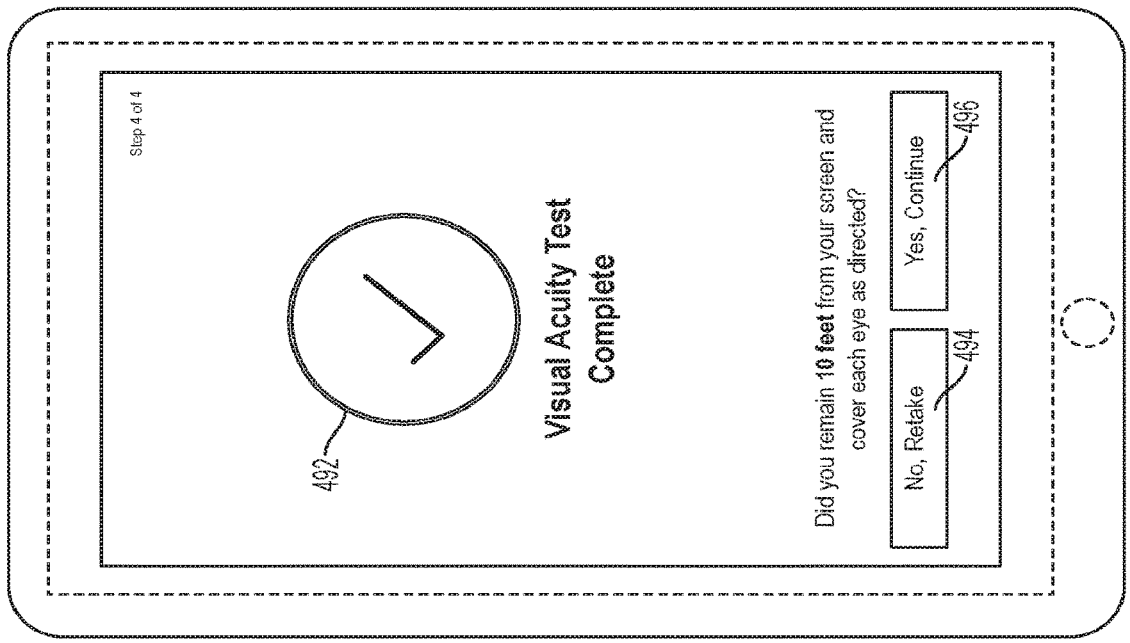

Upon completion of recording user responses to the displayed predetermined optotypes, the vision test app may automatically proceed to display the exemplary GUI screen shown in FIG. 26, which shows a graphic 492 informing the user that the visual acuity test is complete. The exemplary screen also asks the user to confirm that she remained at the predetermined distance, e.g., 10 feet, from the screen 114 of the consumer device 102 and that the user 104 covered the eyes as directed. This GUI screen also includes a touch field 494 that permits the user 104 to answer in the negative and retake the test, and includes a touch field 496 that permits the user to answer in the affirmative and continue. The vision test app may then automatically proceed to display the GUI screen illustrated in FIG. 27, which includes a graphic 498 informing the user that the eye examination is complete, that the test results have been submitted for review, that the physician 112 will review the test results, and that the user's corrective lens order will be shipped upon confirmation by the physician 112 that the test has been passed. In this regard, it may be noted that an attempt to purchase contact lenses may have preceded the visual acuity test and may have, in fact, permitted the user 104 to navigate to the visual acuity test, upon a determination that the user's current prescription for corrective lenses had expired. Reissuance of a corrective lens prescription in this manner may be used to permit a user to purchase contact lenses or spectacles, either online from online optical retailers or in-person at any brick-and-mortar optical retailer.

After the user's spoken responses have been recorded (step 214), as noted at step 216, voice recognition can then be carried out on the audio identifications to generate converted text corresponding to the audio identifications the optotypes spoken by the user 104. Any suitable speech recognition algorithm, such as those conventionally known in the art, may be used in this regard. Additionally, this step can be carried out either at the consumer device 102 or at a remote computer system such as, for example, one or more of the remote computer systems 106, 110. At step 218 of FIG. 2, recognized words of the converted text may be compared to permissible words corresponding to the predetermined optotypes spoken by the user 104 using a lookup table. In this regard, it may be noted, for example, that the lookup table may comprise multiple entries of permissible words for at least a given one of the predetermined optotypes. In other word's, the lookup table may be a multi-to-one lookup table in the sense that speech recognition may yield several, different legitimate words that may correspond to a single given optotype (letter character or other graphic). As an example, Table 1 below illustrates a hypothetical lookup table:

TABLE 1

| O | N | F | D | E | H | R | K | L | C |
|---|---|---|---|---|---|---|---|---|---|
| o | n | f | d | e | h | r | k | l | c |
| oh | nn | eff | dee | ee | ache | are | kay | el | see |
| owe | hen | if | day | he | che | our | chi | elle | sea |
|  | an |  |  |  |  | hour |  | hell | si |

It should be appreciated that a word in this context may include within its scope a single alphabetical letter, e.g., corresponding to an optotype letter of a Snellen chart, and is not limited to multi-letter words. However, if desired, the lookup table may be configured to include only multi-letter words and to exclude single, isolated alphabetical letters.

As shown in Table 1, several potential results of speech recognition might be returned by the speech recognition engine for a given letter-character optotype. Determining whether the user 104 has correctly identified displayed optotypes can be done by taking into account these variations. Also, the lookup table can be updated by carrying out data analytics on visual acuity test results gathered from multiple, e.g., many users 104 who have taken the visual acuity test. In particular, for example, test results from multiple instances of the visual acuity test taken by multiple users 104, and the lookup table may be updated to adjust entries based on the analysis. For instance, it may be determined that certain words should be added to the lookup table and others should be removed based on analysis of user data. It should be understood that both the speech recognition and the lookup table comparison can be carried out at either the consumer device 102 or at a remote computer system such as one or more of remote computer systems 106, 110.

In addition, it should be understood that speech recognition and assessing a user's audible answers for correct responses with a lookup table as noted above is not limited to the example of a visual acuity test utilizing Snellen optotypes. Exemplary visual acuity testing utilizing speech recognition on spoken user responses and lookup tables for evaluating the user's responses can be carried out utilizing any suitable optotypes. For example, Landolt C optotypes, which, as noted above, comprise a sequence of broken rings with gaps presented in different orientations can be used, for instance, in which case the user's spoken responses may identify whether the "C" is "open" or "closed" for sequences of same-size or different-size optotypes, and in which case the a suitable lookup table can be developed to list suitable responses representative of correct answers. In this example, the user 104 could also be prompted to specify whether the gap in "C" is positioned at the "left," "right," "top," or "bottom," and suitable lookup tables can be developed to list a collection of words that represent correct answers. As another example, "tumbling E" optotypes, which, as noted above, comprise "E" shaped symbols with the "fingers" thereof pointing, for a given orientation, in an associated direction, e.g., left, right, up, or down, in which case the user's spoken responses may identify whether the fingers of the "E" positioned pointing "left," "right," "up," or "down" for sequences of same-size or different-size optotypes, and suitable lookup tables can be developed to list a collection of words that represent correct answers. Other optotypes can likewise be used, including but not limited, to geometric symbols (e.g., circle, square, triangle, star, diamond, etc.) and any variety of distinctive shapes such as mathematical symbols (e.g., divided by, plus, times, minus), common objects (ball, scissors, pencil, etc.), fruits (e.g., apple, banana, pear, strawberry, etc.), animal shapes, or any other suitable shapes. Regardless of the optotypes, suitable lookup tables can be prepared to list words that can correspond to correct responses.

In addition, prior to carrying out the portion of the visual acuity test in which optotypes are displayed on the display 114 and the user's audio identifications are recorded, a sound level test can be carried out to determine whether the user's speech and testing conditions are, in fact, sufficient to permit visual acuity testing involving the optotype display portion of the test (before the user 104 undertakes that portion of the test). For example, the user can be instructed to repeat a phrase spoken by the device 102 in order to analyze a speech sample of the user using the microphone 120 of the computerized consumer device 102, with the user 104 and computerized consumer device 102 being separated by the predetermined separation distance range. The computer processor 122a can then calculate a voice quality metric based on audio processing of the speech sample, and determine whether the voice quality metric is sufficient to permit visual acuity testing prior to displaying the predetermined optotypes on the display screen of the computerized consumer device 102. For example, the voice metric may include a sound-level intensity test of the user's voice relative to an ambient sound level, or the voice metric may be a more complex metric, such as involving an analysis of frequencies attributable to the user's voice relative to ambient frequencies. Such a voice quality test prior to presenting the optotypes can improve the consumer experience by avoiding an attempt to collect full test data when sound conditions are not sufficient to do so. If the computer processor 122a determines that the sound conditions are not suitable, it can cause the consumer device 102 to audibly inform the user 104 via the speaker 116 that the test needs to be aborted due to insufficient vocal recognition and audibly inform the user 104 to move to a more quiet location and/or speak more loudly and repeat the test. Reference data for what constitutes sufficient vocal recognition in order for the optotype recognition port of the visual acuity test to proceed can assembled by trial and error testing of various sound levels and/or frequency levels permit speech recognition to be done reliably.

Returning to FIG. 2, at step 220, a score can be determined for the user's visual acuity test based on the comparison of the recognized words of the converted text to permissible words corresponding to the predetermined optotypes. The score can be any suitable numerical score such as a percentage of correct responses, a simple number of correct responses, or a score level determined based on achieving a certain threshold of correct responses. At step 222, a determination can be made regarding whether the user passed the visual acuity test based on the score, e.g., achieved a sufficient number of correct responses to pass. The scoring and the pass/fail determination can be made automatically by the consumer device 102, automatically by a remote computer to which results were communicated such as remote computers 106, 110, and/or by additional review by the screening technician 108 and/or physician 112. At step 224, the outcome of the visual acuity test can be communicated to the user 104 by any suitable means, such as, for example, a subsequent GUI screen at consumer device 102 communicating the outcome (e.g., "you passed"), email, text message, voicemail, regular mail, etc. A copy of the renewed prescription may also be communicated. Where an eye surface test is also being conducted, it may be desirable as a practical matter to report the results of the visual acuity test along with the results of the eye surface test. In that case, where the eye surface test involves review of eye surface imagery (recorded video imagery and/or recorded still imagery) by a physician 112, it may be prefereable to refrain from reporting results of the visual acuity test to the user 104 until the physician 112 has reviewed the eye surface test imagery and rendered a decision on whether the eye test as a whole has been passed, e.g., such that a current prescription may be renewed, and such that the user 104 may proceed to order corrective lenses online.

In addition, in the unlikely event that there are any ambiguities or deficiencies in the test data obtained from the user 104 by the consumer device 102 during the visual acuity test, complete video and audio recordings of the visual acuity test may be captured by the consumer device 102, such that any such ambiguities or deficiencies can be resolved upon review by the screening technician 108 and/or the physician 112. Such review and resolution by medical professionals of any potential deficiencies or ambiguities in test data can improve the customer experience by avoiding a need to instruct the user 104 to repeat the vision test when a repeat of the vision test is not, in fact, necessary. Upon final review and assessment by such medical professionals, test results may then be communicated to the user 104.

Returning to FIG. 2, it was previously mentioned that step 206 relating to carrying out eye surface imaging using the camera 118 of the consumer device 102 would be later described in more detail. That description is now presented. In this regard, FIG. 3 illustrates a flow diagram for an exemplary method 300 for carrying out eye surface imaging according to step 206 of FIG. 2. Reference will also be made to FIGS. 11-16. As shown at step 302 of FIG. 3, the consumer device 102 may receive a user command to commence eye surface imaging with the consumer device 102 to capture imagery of the user's eye surfaces to permit the physician to evaluate any readily apparent conditions of concern, for example, excessive redness in the user's eyes. The exemplary GUI screen in FIG. 11 includes an information portion 422 explaining that this test will use a camera such as camera 118 of the computerized consumer device 102 to photograph the surfaces of the user's eyes, instructing the user to hold the device 102 about 1 foot from the users face, and to turn up the volume on the consumer device 102 and follow the audio prompts. The consumer device 102 may also present these instructions audibly via the speaker 116. The eye-surface imaging test is initiated when the user presses the "begin surface test" field 444 at which point, the vision test app proceeds to display the exemplary GUI screen shown in FIG. 12 on the display screen 114.

Figure 3:
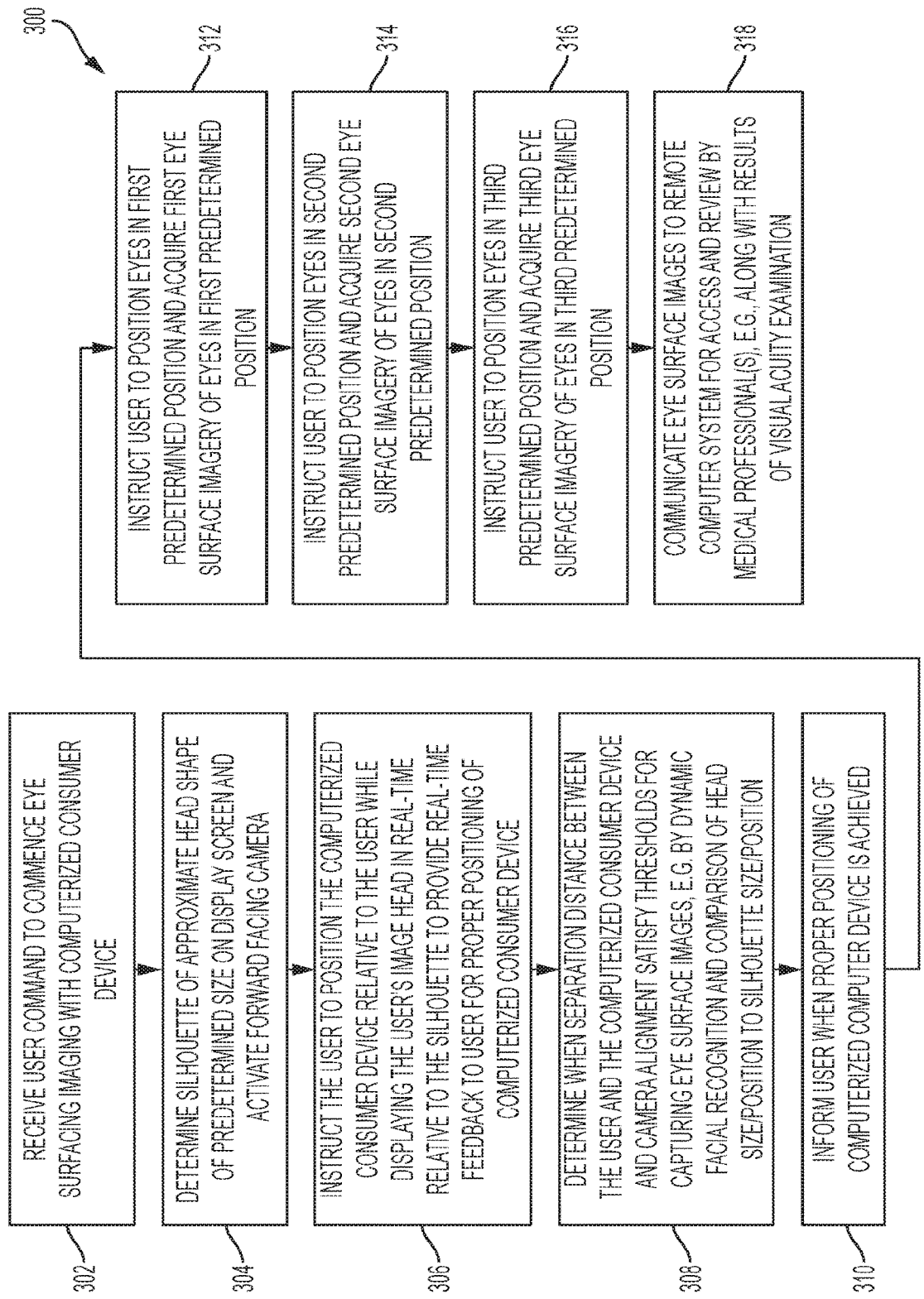
FIG. 3 illustrates a flow diagram for an exemplary approach for carrying out eye surface imaging using a personal computing device according to an exemplary aspect.

As noted at step 304 of FIG. 3 and as illustrated in FIG. 12, the consumer device 102 displays a GUI screen that displays a silhouette graphic 446, e.g., of an approximate head shape, oval, or other suitable outlining shape, of predetermined size on the display screen 114 and activates the (forward facing) camera 118 to begin acquiring and displaying real-time video imagery of the user 104, though the imagery need not necessarily be recorded and stored on a memory at this stage. As noted at step 306, while the real-time imagery of the user 104 is being acquired and displayed on the display screen 114 along with the silhouette 446, the consumer device instructs the user to position the consumer device 102 relative to the user 104, thereby providing real-time visual feedback to the user for proper positioning of the computerized consumer device 102. The computer processor 122a carries out facial detection on the real-time imagery of the user 104 and processes the imagery of the user 104 to determine when the users face is properly positioned relative to the consumer device by being aligned with the silhouette 446. For example, as noted at step 308 the computer processor 122 a can determine when the separation distance between the user 104 and the consumer device 102 and/or camera alignment satisfy thresholds for capturing eye surface images, e.g., when the separation distances is determined to be about 12 inches. For example the computer processor 122 a can carry out dynamic facial detection and compare the head size and position of the imagery of the user 104 to the size and position of the silhouette 446 by analyzing the pixel placements of each, e.g., as mapped to pixels of the image sensor of the camera 118 or as mapped to pixels of the display screen 114. Additionally or alternatively, the computer processor 122 can, for example, detect and monitor the pixel distance between the user's pupils until that distance correspondence corresponds to an expected pixel distance that would be obtained at a 12 inch separation between the consumer device 102 and the user's face, e.g., based on known average or median values of pupillary distance for a population of human subjects. At step 310, the consumer device 102 can inform the user 104, e.g., with an audible and/or visual message, that proper positioning of the consumer device 102 has been achieved relative to the users face and that eye surface imaging will commence.

As shown at step 312 of FIG. 3, the consumer device 102 can instruct the user 104 to position the user's eyes in a first predetermined position, e.g., "Look Left," and can acquire first eye surface imagery of the user's eyes in the first predetermined position using the forward facing camera 118 (or using two or more forward facing cameras to capture such imagery simultaneously from two or more angles or orientations relative to the user's eyes). This imagery may comprise video imagery and/or still imagery. In examples, capturing imagery of the eyes simultaneously from two or more different angles or orientations relative to the user may permit stereoscopic or multiscopic imagery (e.g., video or still imagery) of the eyes to be later viewed by the physician with three-dimensional (3D) depth perception using, e.g., suitable 3D glasses, virtual reality (VR) goggles, and the like. An example of capturing imagery according to step 312 is illustrated by the exemplary GUI screen shown in FIG. 13, which shows the user's head substantially aligned with the silhouette 446 (to within suitable approximation tolerances, such as discussed elsewhere herein), and which shows an instruction portion 452, which in this example states "Look Left." The consumer device 102 may also issue an audio instruction to "Look Left." The consumer device 102 may then capture the eye surface imagery of the user's eyes by either waiting a predetermined time after giving the instruction, e.g., 1 second, 2 second, 3 second, etc., or by detecting proper positioning of the user's eyes using facial detection analysis as described elsewhere herein.

Figure 14:
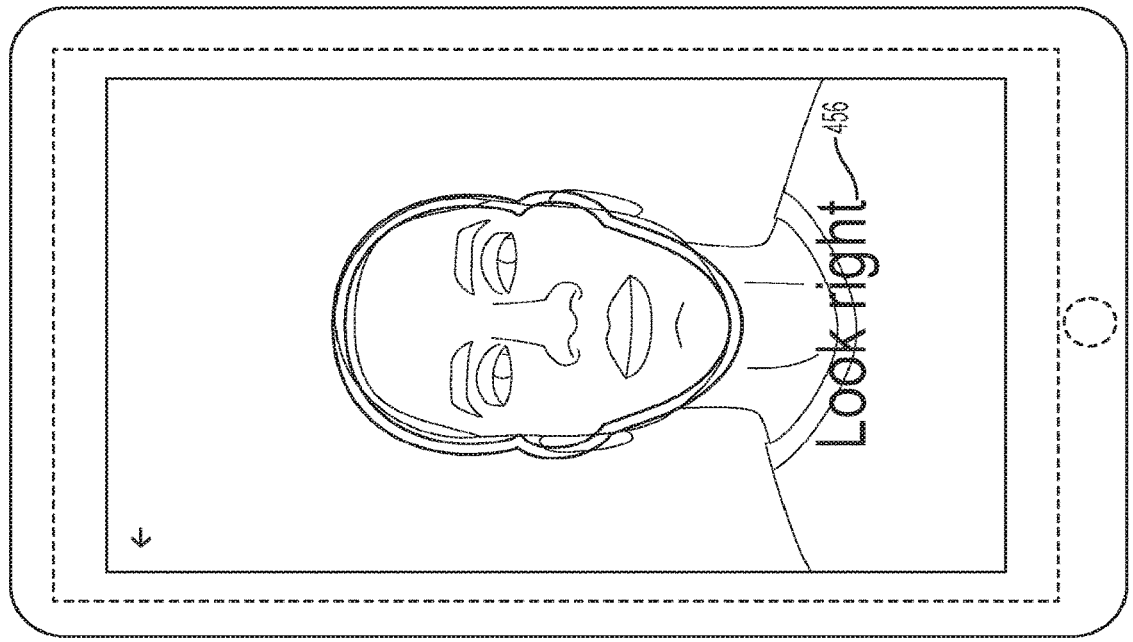

Upon capture of the eye surface imagery in the first predetermined position, the consumer device 102 may automatically proceed to instruct the user 104 to position her eyes in a second predetermined position and acquire second eye surface imagery of the eyes in the second predetermined position (step 314). An example is illustrated in FIG. 14, which shows a GUI screen including the silhouette 446 and superimposed with the real-time imagery of the user 104, and which includes an instruction portion 454 "Look Up." The consumer device 102 may also issue an audio instruction to "Look Up." The consumer device 102 may then capture the eye surface imagery of the user's eyes by either waiting a predetermined time after giving the instruction, e.g., 1 second, 2 second, 3 second, etc., or by detecting proper positioning of the user's eyes using facial detection analysis. This imagery may comprise video imagery and/or still imagery.

Figure 15:
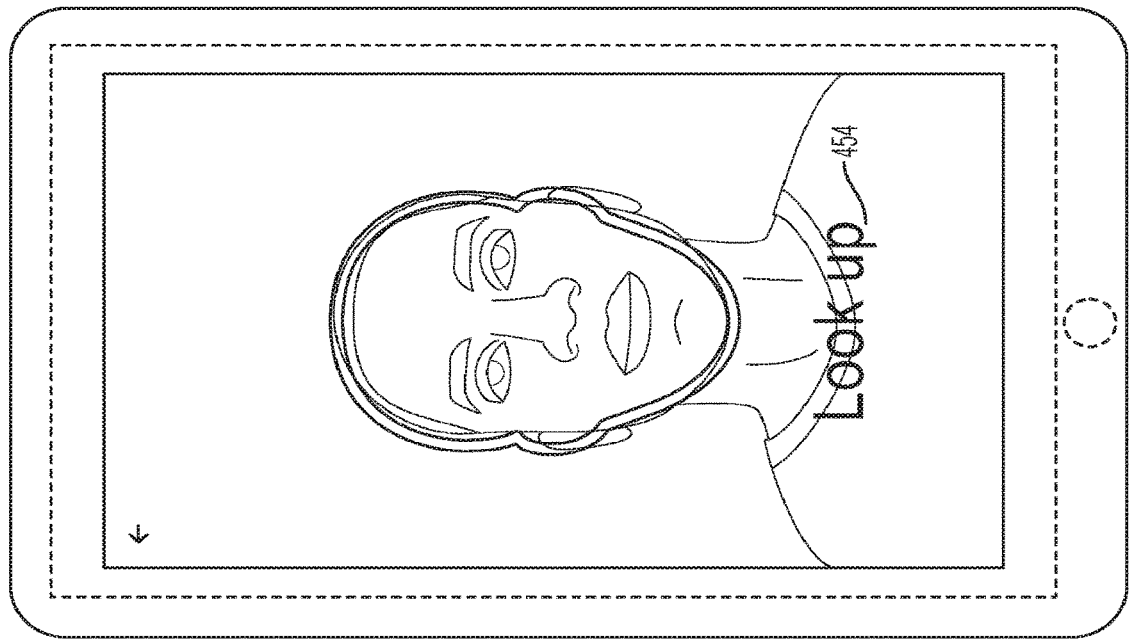

Upon capture of the eye surface imagery in the second predetermined position, the consumer device 102 may automatically proceed to instruct the user to position her eyes in a third predetermined position and acquire third eye surface imagery of the eyes in the third predetermined position (step 316). An example is illustrated in FIG. 15, which shows a GUI screen including the silhouette 446 and superimposed with the real-time imagery of the user 104, and which includes an instruction portion 456 "Look Right." The consumer device 102 may also issue an audio instruction to "Look Right." The consumer device 102 may then capture the eye surface imagery of the user's eyes by either waiting a predetermined time after giving the instruction, e.g., 1 second, 2 second, 3 second, etc., or by detecting proper positioning of the user's eyes using facial detection analysis. This imagery may comprise video imagery and/or still imagery. The imagery of the eye surfaces may then be communicated to remote computer system(s) 1016, 110 for access and review by medical professional(s), such as technician 108 and physician 112, e.g., along with the results (user responses) of the visual acuity examination obtained from the user (step 318).

Figure 16:
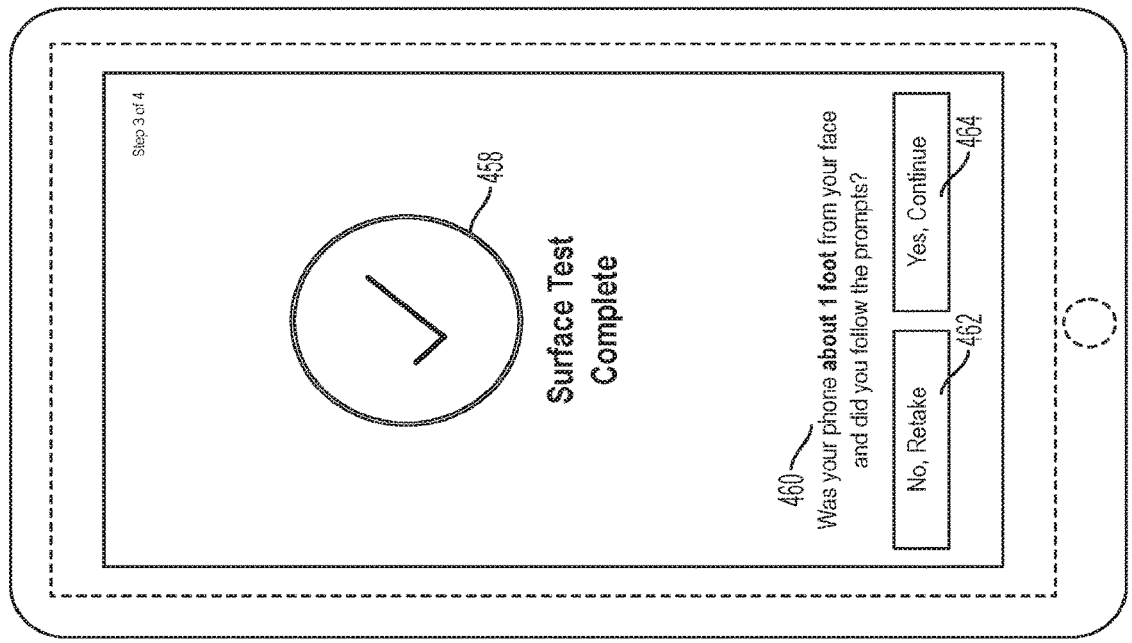

Upon completing the acquisition of the eye surface test imagery of the user's eyes, the vision test app may display the exemplary GUI screen shown in FIG. 16, indicating that the surface test is complete and seeking confirmation from the user 104 of following proper test conditions. For example, the GUI screen may include an information portion 458 that includes a completion graphics such as a checkmark inside a circle accompanied by the language "Surface Test Complete" or "Eye Irritation Check Complete." In addition, the GUI screen may include a question portion 460 asking whether the consumer device 102 was a the designated distance, e.g, about 1 foot, from the user's face and whether the user 104 followed the prompts. Also displayed is a touch field 462 that permits the user to answer in the negative and retake the eye surface test, and a touch field 464 that permits the user to answer in the affirmative and continue. In this example, continuing may comprise moving on to another vision test, such as a visual acuity test as previously described, a colorblindness test, or some other vision test. Alternatively, if the eye surface imaging test is the final test in the series, continuing may comprise completing the testing session and entering an acknowledgment in a touch field such as touch field 499 in FIG. 27 that testing is complete.

In connection with step 318, medical professionals, such as technician 108 and physician 112, may review eye surface imagery of the user's eyes along with user responses (results) of the visual acuity test. As mentioned previously, this imagery may comprise video imagery and/or still imagery, and such imagery of the eyes may be captured simultaneously from two or more different angles or orientations relative to the users. In examples, the physician and technician may therefore review the eye imagery using stereoscopic or multiscopic viewing of video imagery or still imagery of the eyes three-dimensional (3D) depth perception using, e.g., suitable 3D glasses, virtual reality (VR) goggles, and the like. This may permit the physician 112 to view additional perspective information for the imagery of the eye surfaces in assessing whether the corrective lens prescription of the user 104 may be renewed, whether any conditions of potential concern are apparent in the eye surface imagery, and/or may permit the physician 112 to prepare additional recommendations to be communicated to the user 104, such as, for example, informing the user 104 to seek an in-person eye examination at a physician's office.

As noted above, facial detection analysis may be used to detect when the user's eyes are in proper position for eye surface imaging, and this can be beneficial when it is desired to capture high-resolution still images of the surfaces of the user's eyes, which may not be available via recorded real-time video imagery for eye surface imaging. Image analysis for facial detection is generally known in the art, and any suitable facial detection technique may be utilized. For example, Apple's "Vision" API framework may be utilized in iOS devices, and Google's "Face" API framework for Android devices to detect a user's face and features thereof relative to other scene imagery. In addition, face detection and analysis algorithms, such as OpenCV (Open Source Computer Vision Library) known in the art may be used to detect a user's face and features thereof relative to other scene imagery. After detecting the user's eyes, image processing can be used to detect the portions of white color at the user's imaged eyes at a lateral left half of the eye and a lateral right half of the eye in order to determine whether such measurements satisfy one or more thresholds to determine that the user's eyes are pointing sufficiently right or sufficiently left in order to acquire eye surface images at those predetermined positions. Alternatively, or in addition, image processing may be used to detect the position of the black pupils of the user's eyes to determine whether a given position of a pupil satisfies a right-position threshold or a left-position threshold to determine that the user's eyes are pointing sufficiently right or sufficiently left in order to acquire eye surface images at those predetermined positions. Likewise such APIs can be utilized, after detecting the user's eyes, to detect the proportion of white color at the user's imaged eyes at a lower half (or upper half) of the eyes in order to determine whether that proportion satisfies a threshold to determine that the user's eyes are pointing sufficiently up (or down) in order to acquire eye surface images and those predetermined positions. While such measurements may be made for both eyes of the user 104, it should be understood that such a measurement or measurements for one eye of the user 104 may suffice, because both eyes are expected to move in unison. Additional information regarding known facial recognition technology that may be applicable is disclosed, for example, in Yang et al., "Detecting faces in images: A survey," IEEE Transactions on Pattern Analysis and Machine Intelligence, Vol. 24, No. 1, 2002, pp. 34-58, Hjelmas et al., "Face detection: A Survey," Computer Vision and Image Understanding, Vol. 83, No. 3, 2001, pp. 236-274, and U.S. Pat. Nos. 9,832,452, 9,053,354, 8,811, 726, 8,442,327, 8,254,691, and 7,372,981, the entire contents of each of which are incorporated herein by reference.

The methods and systems described herein may be implemented using any suitable computer processing system with any suitable combination of hardware, software and/or firmware. As shown in FIG. 1, for example, computerized consumer devices 102 with which users 104 can take vision tests can communicate with remote computer systems 106 and 110 as well as computer servers 130 that may access databases 132 via network 134. Remote computer system 106 and 110 may also be hosted on one or more computer servers 130 via a network such as network 134. The computer processors 122a, 122b, 122c, etc., may execute software operations, program instructions or routines to implement calculations and analyses described herein. Such program instructions, accumulated data, and processed data may be stored one or more non-transitory computer-readable memories 124a, 124b, 124c, using databases 128b, 128c, 132, etc. Communications may be carried out according to a client server architecture whereby computerized consumer devices 102 used by users 104 access the remote computer systems 106, 100 and/or server computers 130 via one or more networks 134.

The systems may include element managers, real-time data buffers, conveyors, file input processors, database indices, data buffers and data managers for managing data and processing. The systems 102, 106, 110 may also include multiple displays, display interfaces, input/output devices such as a keyboards, microphones, mice, touch screens and the like for permitting users, support personnel, and medical personnel to manage the systems 102, 106, 110.

This written description describes exemplary embodiments of the invention, but other variations fall within scope of the disclosure. For example, the systems and methods may include and utilize data signals conveyed via networks (e.g., local area network, wide area network, internet, combinations thereof, etc.), fiber optic medium, carrier waves, wireless networks, etc. for communication with one or more data processing devices. The data signals can carry any or all of the data disclosed herein that is provided to or from a device.

The methods and systems described herein may be implemented on many different types of processing devices by program code comprising program instructions that are executable by the device processing system. The software program instructions may include source code, object code, machine code, or any other stored data that is operable to cause a processing system to perform the methods and operations described herein. Any suitable computer languages may be used such as C, C++, Java, HTML, XML, etc., as well as APIs available to developers for given operating system platforms, as will be appreciated by those skilled in the art. Other implementations may also be used, however, such as firmware or even appropriately designed hardware configured to carry out the methods and systems described herein.

The systems' and methods' data (e.g., associations, mappings, data input, data output, intermediate data results, final data results, etc.) may be configured for storage using any suitable data structures, and may be stored and implemented in one or more different types of computer-implemented data stores, such as different types of storage devices and programming constructs (e.g., RAM, ROM, Flash memory, flat files, databases, programming data structures, programming variables, IF-THEN (or similar type) statement constructs, etc.). It is noted that data structures describe formats for use in organizing and storing data in databases, programs, memory, or other non-transitory computer-readable media for use by a computer program.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. In addition, as used in the description herein and throughout the claims that follow, the meanings of "and" and "or" include both the conjunctive and disjunctive and may be used interchangeably unless the context expressly dictates otherwise; the phrase "exclusive or" may be used to indicate situation where only the disjunctive meaning may apply. In addition, as used in the description herein and throughout the claims that follow, the meaning of "about" and/or "approximately" refers to ±10% of the quantity indicated, unless otherwise indicated.

While the present invention has been described in terms of exemplary embodiments, it will be understood by those skilled in the art that various modifications can be made thereto without departing from the scope of the invention as set forth in the claims.

What is claimed is:

1. A method for testing visual acuity of a user using a computerized device, the method comprising:
    initiating a visual acuity test to assess the visual acuity of a user using a computerized device, the computerized device comprising a display screen, a camera, a microphone, a speaker, a computer processor, and a memory;
    determining, by the computerized device, a separation distance between a user and the computerized device based on an image size of a physical feature of the user using imagery of the user taken by the camera of the computerized device;
    instructing, by the computerized device, the user to adjust the separation between the user and the computerized device to a predetermined separation distance range;
    presenting, by the computerized device, a visual acuity test to the user without use of a refractor lens assembly, wherein presenting the visual acuity test comprises displaying predetermined optotypes at the display screen of the computerized device for the user to perceive;
    recording, at the computerized device, identifications by the user of perceptions of the predetermined optotypes; and
    determining a score for visual acuity test taken by the user based on the identifications.

2. The method of claim 1, further comprising:
    displaying a silhouette of an approximate head shape of predetermined size on the display screen and activating the camera;
    instructing the user to position the computerized device relative to the user while displaying the user's imaged head in real-time relative to the silhouette to provide real-time feedback to user for proper positioning of computerized device;
    determining that at least one of a separation distance between the user and the computerized device and a camera alignment relative to the user's face satisfy thresholds for capturing eye surface images; and
    capturing imagery of eye surfaces of the user's eyes using the camera of the computerized device.

3. The method of claim 2, wherein capturing the imagery of the eye surfaces of the user's eyes comprises:
processing imagery of the user's eyes by real-time image analysis to detect that an orientation of the user's eyes are in a proper position;
acquiring still imagery of the user's eyes with the user's eyes in the proper position; and
storing the still imagery for designation as eye-surface imagery.

4. The method of claim 2, wherein capturing the imagery of the eye surfaces of the user's eyes comprises capturing the imagery of the eye surfaces simultaneously from multiple cameras at the computerized device, the multiple cameras being spaced apart from one another to thereby obtain the imagery of the eye surfaces from multiple different orientations.

5. The method of claim 1, comprising:
acquiring a speech sample of the user using the microphone of the computerized device with the user and computerized device being separated by the predetermined separation distance range;
calculating a voice quality metric based on audio processing of the speech sample; and
determining whether the voice quality metric is sufficient to permit visual acuity testing prior to displaying the predetermined optotypes on the display screen of the computerized device.

6. The method of claim 1, comprising suspending an automated brightness control of the display of the computerized device prior to presenting the visual acuity test.

7. The method of claim 1, wherein displaying predetermined optotypes at the display screen of the computerized device is carried out without changing a size of the predetermined optotypes displayed on the display screen based on the separation distance between the user and the computerized device determined by the computerized device.

8. The method of claim 1, wherein the computerized device comprises a tablet computer, a smart phone, or a personal computer.

9. A system for carrying out a visual acuity test of a user, comprising:
a computerized device, the computerized device including:
a display screen,
a camera,
a microphone,
a speaker,
a computer processor,
and a memory,
the computer processor being configured to cause the computerized device to:
initiate a visual acuity test to assess the visual acuity of a user using the computerized device;
determine a separation distance between a user and the computerized device based on an image size of a physical feature of the user using imagery of the user taken by the camera of the computerized device;
instruct the user to adjust the separation between the user and the computerized device, and instruct the user that a predetermined separation distance range is achieved;
present a visual acuity test to the user without use of a refractor lens assembly, wherein presenting the visual acuity test comprises displaying predetermined optotypes at the display screen of the computerized device for the user to perceive;
receive identifications by the user of perceptions of the predetermined optotypes via the computerized device;
and
determine a score for the visual acuity test taken by the user based on said received identifications.

10. The system of claim 9, the computer processor being further configured to cause the computerized device to:
display a silhouette of an approximate head shape of predetermined size on the display screen;
activate the camera;
instruct the user to position the computerized device relative to the user while displaying the user's imaged head in real-time relative to the silhouette to provide real-time feedback to user for proper positioning of computerized device;
determine that at least one of a separation distance between the user and the computerized device and a camera alignment relative to the user's face satisfy thresholds for capturing eye surface images; and
capture imagery of eye surfaces of the user's eyes using the camera of the computerized device.

11. The system of claim 10, the computer processor being further configured to cause the computerized device to capture the imagery of the eye surfaces of the user's eyes by:
processing imagery of the user's eyes by real-time image analysis to detect that an orientation of the user's eyes are in a proper position;
acquiring still imagery of the user's eyes with the user's eyes being in the proper position; and
storing the still imagery for designation as eye-surface imagery.

12. The system of claim 10, the computer processor being further configured to cause the computerized device to capture the imagery of the eye surfaces of the user's eyes by capturing the imagery of the eye surfaces simultaneously from multiple cameras at the computerized device, the multiple cameras being spaced apart from one another.

13. The system of claim 9, the computer processor being further configured to cause the computerized device to:
acquire a speech sample of the user using the microphone of the computerized device with the user and computerized device being separated by the predetermined separation distance range;
calculate a voice quality metric based on audio processing of the speech sample;
and
determine whether the voice quality metric is sufficient to permit visual acuity testing prior to displaying the predetermined optotypes on the display screen of the computerized device.

14. The system of claim 9, the computer processor being further configured to cause the computerized device to suspend an automated brightness control of the display of the computerized device prior to presenting the visual acuity test.

15. The system of claim 9, the display of the predetermined optotypes at the display screen of the computerized device being carried out without changing a size of the predetermined optotypes displayed on the display screen based on the predetermined separation distance range.

16. The system of claim 9, wherein the computerized device comprises a tablet computer, a smart phone, or a personal computer.

17. A non-transitory computer readable medium comprising program instructions for permitting a computerized device to carry out a visual acuity test of a user, the program instructions when executed causing a computer processor of the computerized device to:

initiate a visual acuity test to assess the visual acuity of a user using the computerized device, the computerized device including a display screen, a camera, a microphone, a speaker, a computer processor, and a memory;

determine a separation distance between a user and the computerized device based on an image size of a physical feature of the user using imagery of the user taken by the camera of the computerized device;

instruct the user to adjust the separation between the user and the computerized device to a predetermined separation distance range;

present a visual acuity test to the user without use of a refractor lens assembly, wherein presenting the visual acuity test comprises displaying predetermined optotypes at the display screen of the computerized device for the user to perceive;

receive identifications by the user of perceptions of the predetermined optotypes via the computerized device; and determine a score for visual acuity test taken by the user based on said received identifications.

18. The non-transitory computer readable medium of claim 17, the program instructions being further configured to cause the computer processor to control the computerized computer device to:

display a silhouette of an approximate head shape of predetermined size on the display screen;

activate the camera;

instruct the user to position the computerized device relative to the user while displaying the user's imaged head in real-time relative to the silhouette;

determine that at least one of a separation distance between the user and the computerized device and a camera alignment relative to the user's face satisfy thresholds for capturing eye surface images; and capture imagery of eye surfaces of the user's eyes using the camera of the computerized device.

19. The non-transitory computer readable medium of claim 18, the program instructions being further configured to cause the computer processor to control the computerized computer device to capture the imagery of the eye surfaces of theuser's eyes by:

processing imagery of the user's eyes by real-time image analysis to detect that an orientation of the user's eyes are in a proper position;

acquiring still imagery of the user's eyes with the user's eyes being in the proper position; and storing the still imagery for designation as eye-surface imagery.

20. The non-transitory computer readable medium of claim 18, the program instructions being further configured to cause the computer processor to control the computerized device to capture the imagery of the eye surfaces of the user's eyes by capturing the imagery of the eye surfaces simultaneously from multiple cameras at the computerized device, the multiple cameras being positioned to obtain the imagery of the eye surfaces from multiple different orientations.

21. The non-transitory computer readable medium of claim 17, the program instructions being further configured to cause the computer processor to control the computerized computer device to:

acquire a speech sample of the user using the microphone of the computerized device with the user and computerized device being separated by the predetermined separation distance range;

calculate a voice quality metric based on audio processing of the speech sample; and determine whether the voice quality metric is sufficient to permit visual acuity testing prior to displaying the predetermined optotypes on the display screen of the computerized device.

22. The non-transitory computer readable medium of claim 17, the program instructions being configured to cause the computer processor to control the computerized computer device to suspend an automated brightness control of the display of the computerized device prior to presenting the visual acuity test.

23. The non-transitory computer readable medium of claim 17, the program instructions being further configured to cause the computer processor to control the computerized device to display the predetermined optotypes at the display screen of the computerized device without changing a size of the predetermined optotypes displayed on the display screen based on the predetermined separation distance range.

24. The non-transitory computer readable medium of claim 17, wherein the computerized device comprises a tablet computer, a smart phone, or a personal computer.

25. A method for testing visual acuity of a user, comprising:

initiating a visual acuity test using a computerized device, the computerized device comprising a display screen, a camera, an audio interface including a microphone and a speaker, a computer processor, and a memory, the visual acuity test comprising a graphical interface for displaying information to the user and for receiving input from the user via touch sensitive fields;

determining distance information of a measured distance between the computerized device and the user measured from imagery of the user captured by the camera of the computerized device, the graphical interface being configured to dynamically display the distance information in real time as the measured distance changes;

displaying, via the graphical interface, the visual acuity test without use of a refractor lens assembly including displaying predetermined optotypes for the user to perceive, and presenting audio instructions for the visual acuity test via the speaker of the audio interface;

recording, via the microphone of the audio interface, spoken identifications by the user of perceptions of the predetermined optotypes;

carrying out speech recognition on the user's spoken identifications to generate converted text corresponding to the spoken identifications; and determining a score for visual acuity test taken by the user based on said converted text.

26. The method of claim 25, comprising:

displaying, via the graphical interface, a silhouette of an approximate head shape of predetermined size superimposed with imagery of the user acquired in real-time with the camera to provide real-time feedback to user for proper positioning of the computerized device;

determining that at least one of a separation distance between the user and the computerized device and a camera alignment relative to the user's face satisfy thresholds for capturing eye surface images;

notifying the user of achieving the proper positioning; and
capturing imagery of eye surfaces of the user's eyes using the camera of the computerized device.

27. The method of claim 26, comprising capturing the imagery of the eye surfaces simultaneously from multiple cameras at the computerized device, the multiple cameras being configured to obtain the imagery of the eye surfaces from multiple different orientations.

* * * * *